US009970929B2

(12) United States Patent
Valdez et al.

(10) Patent No.: US 9,970,929 B2
(45) Date of Patent: May 15, 2018

(54) VORICONAZOLE IMMUNOASSAYS

(71) Applicant: ARK Diagnostics, Inc., Fremont, CA (US)

(72) Inventors: Johnny Valdez, Fremont, CA (US); Soon J. Oh, Sunnyvale, CA (US); Byung Sook Moon, Palo Alto, CA (US)

(73) Assignee: ARK Diagnostics, Inc., Fremont, CA (US)

( * ) Notice: Subject to any disclaimer, the term of this patent is extended or adjusted under 35 U.S.C. 154(b) by 337 days.

(21) Appl. No.: 14/158,485

(22) Filed: Jan. 17, 2014

(65) Prior Publication Data

US 2014/0206020 A1  Jul. 24, 2014

Related U.S. Application Data

(60) Provisional application No. 61/754,187, filed on Jan. 18, 2013.

(51) Int. Cl.
G01N 33/53 (2006.01)

(52) U.S. Cl.
CPC ............................ G01N 33/5308 (2013.01)

(58) Field of Classification Search
CPC .................................................. G01N 33/5308
See application file for complete search history.

(56) References Cited

U.S. PATENT DOCUMENTS

| | | | |
|---|---|---|---|
| 3,817,837 A | 6/1974 | Rubebstein et al. | |
| 3,875,011 A | 4/1975 | Rubenstein et al. | |
| 4,492,762 A | 1/1985 | Wang et al. | |
| 4,708,929 A | 11/1987 | Henderson | |
| 4,816,567 A | 3/1989 | Cabilly et al. | |
| 4,857,453 A | 9/1989 | Ullman et al. | |
| 4,868,131 A | 9/1989 | Hiratsuka | |
| 5,851,829 A | 12/1998 | Marasco et al. | |
| 5,965,371 A | 10/1999 | Marasco et al. | |
| 6,455,288 B1 | 9/2002 | Jakobovits et al. | |
| 6,514,770 B1 | 2/2003 | Sorin | |
| 6,784,197 B2 | 8/2004 | Differding et al. | |
| 7,037,939 B2 | 5/2006 | Hwang | |
| 7,101,980 B2 | 9/2006 | Hui et al. | |
| 7,169,907 B2 | 1/2007 | Hui | |
| 7,183,259 B2 | 2/2007 | Scheueman et al. | |
| 7,202,092 B2 | 4/2007 | Ghoshal et al. | |
| 7,205,116 B2 | 4/2007 | Salamone et al. | |
| 7,271,252 B2 | 9/2007 | Sigler et al. | |
| 7,358,276 B2 | 4/2008 | Differding et al. | |
| 8,168,756 B2 | 5/2012 | Valdez et al. | |
| 2002/0058656 A1 | 5/2002 | Ockert | |
| 2002/0098999 A1 | 7/2002 | Gallop et al. | |
| 2002/0111338 A1 | 8/2002 | Cundy et al. | |
| 2002/0151529 A1 | 10/2002 | Cundy et al. | |
| 2003/0158254 A1 | 8/2003 | Zerangue et al. | |
| 2003/0181390 A1 | 9/2003 | Gallop et al. | |
| 2004/0248811 A1 | 12/2004 | Hwang et al. | |
| 2004/0254344 A1 | 12/2004 | Gallop et al. | |
| 2005/0148564 A1 | 7/2005 | Cundy et al. | |
| 2005/0228035 A1 | 10/2005 | Feuerstein et al. | |
| 2005/0244816 A1 | 11/2005 | Valdez | |
| 2005/0272710 A1 | 12/2005 | Cundy et al. | |
| 2005/0288228 A1 | 12/2005 | Cundy et al. | |
| 2006/0115865 A1* | 6/2006 | Ouyang ............... | C07D 249/14 435/7.92 |
| 2006/0141548 A1 | 6/2006 | Roberts et al. | |
| 2007/0135356 A1 | 6/2007 | Scheueman et al. | |
| 2008/0009018 A1 | 1/2008 | Ouyang et al. | |
| 2008/0199887 A1 | 8/2008 | Valdez et al. | |
| 2009/0093069 A1 | 4/2009 | Valdez et al. | |
| 2010/0173427 A1 | 7/2010 | Valdez et al. | |
| 2011/0105448 A1 | 5/2011 | Dhuppad et al. | |

FOREIGN PATENT DOCUMENTS

| | | |
|---|---|---|
| EP | 0659751 | 6/1995 |
| EP | 1470825 | 10/2004 |
| WO | 9700248 | 1/1997 |
| WO | WO 9733858 | 9/1997 |
| WO | WO 0050027 | 8/2000 |
| WO | WO 2001062726 | 8/2001 |
| WO | WO 0228883 | 4/2002 |
| WO | WO 0242414 | 5/2002 |
| WO | WO 0300642 | 1/2003 |
| WO | WO 07065036 | 6/2007 |
| WO | 2008097640 | 8/2008 |
| WO | 2011020605 | 2/2011 |
| WO | 2012172015 | 12/2012 |

OTHER PUBLICATIONS

Howard et al., "Clinical application of voriconazole concentrations in the treatment of invasive aspergillosis," Ann. Pharmacother., 2008, vol. 42, issue 12, pp. 1859-1864.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Oh et al., "ARKTM Homogeneous Enzyme Immunoassays for Voriconazole and Posaconazole" posted on Internet on Sep. 19, 2013 (http://www.temaricerca.com/entry2013new/admindia/ckfinder/userfiles/files/IATDMCT_poster_11x17_091713.pdf).*
Englebienne, "Immune and Receptor Assays in Theory and Practice," CRC Press, 2000, p. 308.*
Contin et al., "Levetiracetam Therapeutic Monitoring in Patients with Epilepsy Effect of Concomitant Antiepileptic Drugs," *Ther Drug Monit*. 26(4): 375-379(2004).
Engvall "Enzyme immunoassay ELISA and EMIT," *Methods Enzymol* 70:419-439 (1980).
Gunther, et al., "QMS Levetiracetam Assay on the Hitachi 917 System," Clinical Chemistry, 55(6): Supplement, Abstract E-167 (2009).

(Continued)

*Primary Examiner* — Galina Yakovleva

(74) *Attorney, Agent, or Firm* — Rudy J. Ng; Bozicevic, Field & Francis LLP

(57) ABSTRACT

Methods, compositions and kits are disclosed directed at voriconazole derivatives, immunogens, signal generating moieties, antibodies that bind voriconazole and immunoassays for detection of voriconazole.

16 Claims, 9 Drawing Sheets

(56) References Cited

OTHER PUBLICATIONS

Hurwitz, et al., "Levetiracetam Induced Interstitial Nephritis and Renal Failure," Pediatr. Neurol, 41:57-58 (2009).
Kenda, et al.; "Discovery of 4-Substituted Pyrrolidone Butanamides as New Agents with Significant Antiepileptic Activity," *J. Med. Chem.*, 47(3):530-535 (2004).
Kohler and Milstein,"Continuous cultures of fused cells secreting antibody of predefined specificity," Nature, 256: 495-497 (1975).
Mayer, et al., "Luminescent Label-ore than just an alternative to radioisotopes?" *Angewandte Chemie*, 33(10), 1044-1072 (1994).
McCafferty, et al., "Phage antibodies: filmentous phage displaying antibody variable domains," *Nature* 348:552-554 (1990).
Nolli, et al., "Antibodies against the antibiotics: an overview," *Ann. 1st Super Sanita*, 27(1):149-154 (1991).
Noyer, et al. "The Novel Antiepileptic Drug Levetiracetam (ucb L059) Appears to Act via a Specific Binding Site in CNS Membranes" *Eur. J. Pharmolcol*. 286(2):137-146 (1995).
Roffey, et al., "The Disposition of Voriconazole in Mouse, Rat, Rabbit, Guinea Pig, Dog, and Human" *Drug Metabolism and Disposition*, 31(6):731-781 (2003).
Sargentini-Maier, et al., "Pharmacokinetics and Metabolism of 14C-Brivaracetam, a Novel SV2A Ligand, in Healthy Subjects" *Drug Metab. Dispos*. ,36(1):36-45 (2008).
Urdabayev and Uoyang "Novel Levetiracetam Derivatives for Immunoassay" The 236th ACS National Meeting, Philadelphia, Proposed Activities, Aug. 17-21, Abstract Published Online (2008).
Williams, et al., Interlaboratory variability in the quantification of new generation antieoileptic drugs based on External quality assessment data. Epilepsia, 44(1):40-45 (2003).
Warrilow, et al., "Identification, Characterization, and Azole-Binding Properties of *Mycobacterium smegmatis* CYP16A2, a Homolog of ML2088 the Sole Cytochrome P450 Gene of *Mycobacterium leprae*" Antimibrob. Agents Chemother 56(3): 1157-1164 (2009).

Na, "Synthesis and Activity of Novel 1-Halogenobenzylindole Linked Triazole Derivatives as Antifungal Agents" Bull. Chem Soc. 32(1): 307-310 (2011).
Feng et al. "Structural characterization of the oxidative degradation products of an antifungal agent SCH 56592 by LC-NMR and LC-MS." J. of Pharm and Biom. Analysis 25 (3-4): 545-557 (2001).
Steinmann et al., "Comparison and evaluation of a novel bioassay and high-performance liquid chromatography for the clinical measurement of serum voriconazole concentration," Mycoses 54(5) e421-e428 (2010).
Cendejas-Bueno et al., "HPLC/UV or bioassay: two valid methods for posaconazole quantification in human serum samples," Clin. Microbiol. Infect., 18(12) 1229-1235 (2012).
Chen et al., "Development of an Enzyme-Linked Immunosorbent Assay for a Broad Spectrum Triazole Fungicide: Hexaconazole" J. Agric. Food Chem 44 1352-1356 (1996).
Coachman et al., "An automated method for the simultaneous measurement of azole antifungal drugs in human plasma or serum using turbulent flow liquid chromatography-tandem mass spectrometry" Anal Bioanal Chem. 404:513-523 (2012) XP035083685.
Manclus et al., "Development of Monoclonal Immunoassays for the Determination of Triazole Fungicides in Fruit Juices," J. Agric. Food Chem. 56: 8793-8800 (2008) XP055291307.
Nagappan et al., "Posaconazole: A Broad-Spectrum Triazole Antifungal Agent" Clinical Infectious Diseases 45(12)1610-1617 (2007).
Schiller et al., "Posaconazole: An extended-spectrum triazole antifungal agent," Clinical Therapeutics, Excerpta Medica Princeton 29(9) 1862-1886 (2007) XP022354377.
Sharma & Bhatia "Triazoles in Antifungal Therapy: A Review" International Journal of Research in Pharmaceutical and Biomedical Science 2(2): 417-427 (2011) XP055291413.
Szurdoki et al., (1995) "Important Factors in Hapten Design and Enzyme-Linked Immunosorbent Assay Development," in Immunoanalysis of Agrochemicals: Nelson, J., et al.: ACS Symposium Series, 586(4) 39-63.

* cited by examiner

VORICONAZOLE IMMUNOASSAYS

CROSS-REFERENCE TO RELATED APPLICATION

Pursuant to 35 U.S.C. § 119 (e), this application claims priority to the filing date of U.S. Provisional Patent Application Ser. No. 61/754,187 filed on Jan. 18, 2013, the disclosure of which is herein incorporated by reference.

INTRODUCTION

Voriconazole is a second-generation triazole antifungal agent. Voriconazole is a broad-spectrum triazole antifungal used for the treatment of invasive fungal infections. Voriconazole is designated chemically as (2R,3S)-2-(2,4-difluorophenyl)-3-(5-fluoro-4-pyrimidinyl)-1-(1H-1,2,4-triazol-1-yl)-2-butanol with an empirical formula of $C_{16}H_{14}F_3N_5O$ and a molecular weight of 349.3, and has the following chemical structure:

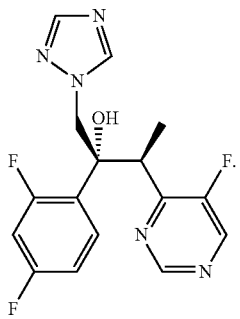 [SMILES: C[C@@H](c1ncncc1F)[C@](O)(Cn1cncn1)c1ccc(F)cc1F]

Voriconazole therapeutic drug monitoring (TDM) has been advocated during treatment of invasive fungal infections to optimize efficacy and minimize toxicity and intolerance and routine TDM of voriconazole may reduce drug discontinuation due to adverse events and improve the treatment response in invasive fungal infections. (Pascual and Marchetti, *Antimicrob. Agents Chemother.* 2009; 53:24-34; Park et al., *Clin Infect Dis.* 2012; 55(8):1080-7; Brüggemann et al., *Ther Drug Monit*, 30:403-411, 2008). In a randomized control study, it was shown that routine TDM of voriconazole may reduce drug discontinuation due to adverse events and improve the treatment response in invasive fungal infections (Park et al., *Clin Infect Dis.* 2012; 55(8):1080-7). An evolving body of evidence also suggests voriconazole TDM for children (Chen et. al., *Ther Drug Monit*, 34:77-84, 2012).

As such, there is a need in the art for immunoassays for routine measurement of voriconazole in human biological fluids of patients treated with voriconazole.

SUMMARY

Methods, compositions and kits are disclosed directed at voriconazole derivatives, immunogens, signal generating moieties, antibodies that bind voriconazole and immunoassays for detection of voriconazole.

The embodiments provide for detection of voriconazole in a sample. A variety of haptens, hapten-reactive partner conjugates, hapten derivatives, receptors, methods, and kits are useful in this determination.

Embodiments of the present disclosure include a compound of the formula 1:

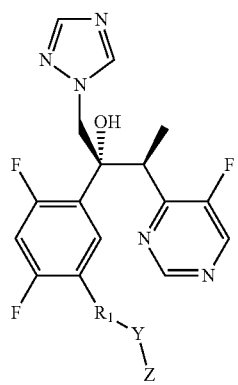

wherein
$R_1$ is —NH, —NHCO, —SH or —O;
Y is a linking group; and
Z is selected from the group consisting of hydrogen, —OH, —SH, —S-acyl; —O-lower alkyl, halogen, —NH$_2$, epoxy, maleimidyl, haloacetamide, carboxyl, activated carboxyl, an immunogenic carrier, a protein, and a label, and
salts thereof.

Embodiments of the present disclosure also include a compound of the formula 2:

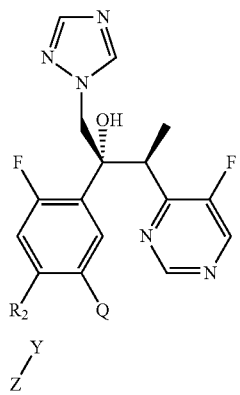

wherein
Q is —NO$_2$;
$R_2$ is —NH; —NHCO; —SH or —O;
Y is a linking group; and
Z is selected from the group consisting of hydrogen, —OH, —SH, —S-acyl; —O-lower alkyl, halogen, —NH$_2$, epoxy, maleimidyl, haloacetamide, carboxyl, activated carboxyl, an immunogenic carrier, a protein, and a label, and
salts thereof.

Aspects of the present disclosure include a method for detecting voriconazole. The method includes combining in a reaction mixture a sample suspected of containing voriconazole with an antibody that binds a compound of formula 1 or 2. The method further includes detecting the presence or absence of a complex of voriconazole and the antibody, where the presence of the complex indicates the presence of voriconazole in the sample. In some embodiments, the reaction mixture further includes a labeled conjugate of a compound of formula 1 or 2.

Aspects of the present disclosure include an isolated antibody that binds an epitope present in voriconazole and present in a compound of formulae 1 or 2. In some embodiments, the antibody is a polyclonal antibody or a monoclonal antibody. In some embodiments, the antibody does not detectably bind voriconazole N-oxide. In some embodiments, the antibody has a cross-reactivity with voriconazole N-oxide of 10% or less with respect to binding to voriconazole. In some embodiments, the antibody has a cross-reactivity with fluconazole, itraconazole and posaconazole of 5% or less each with respect to binding to voriconazole.

Aspects of the present disclosure include a kit for detecting voriconazole in a sample. The kit includes: (a) an antibody that binds an epitope present in voriconazole and present in a compound of formulae 1 or 2; and (b) optional ancillary reagents for detecting a complex of the antibody and voriconazole. In some embodiments, the kit further includes a labeled conjugate of a compound of formulae 1 or 2. The antibody of the kit may be an antibody raised against a compound of formulae 1 or 2 above.

DEFINITIONS

Figure 1:
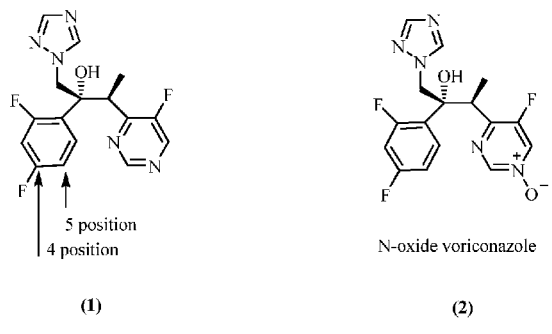
FIG. 1 shows chemical structures for: voriconazole (1), which is designated chemically as (2R,3S)-2-(2,4-difluorophenyl)-3-(5-fluoro-4-pyrimidinyl)-1-(1H-1,2,4-triazol-1-yl)-2-butanol, and voriconazole N-oxide metabolite (2), which is designated chemically as 4-((2S,3R)-3-(2,4-difluorophenyl)-3-hydroxy-4-(1H-1,2,4-triazol-1-yl)butan-2-yl)-5-fluoropyrimidine 1-oxide.
Figure 2:
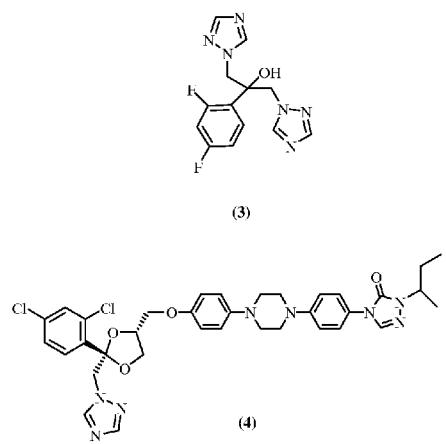
FIG. 2 shows chemical structures for the triazole antifungal drugs: Fluconazole (3), Itraconazole (4), and Posaconazole (5).
Figure 2:
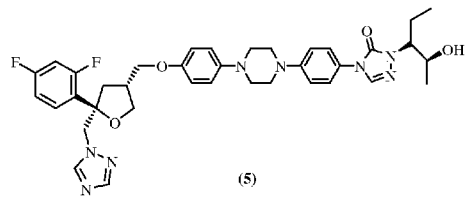

Unless defined otherwise, all technical and scientific terms used herein have the same meaning as commonly understood by one of ordinary skill in the art to which the present disclosure is related. The following terms are defined for purposes of the present disclosure.

Analyte

An analyte is the compound or composition to be measured, the material of interest, such as voriconazole. In certain embodiments, the analyte is a member of a specific binding pair (sbp) and may be a ligand, which is mono- or polyvalent, may be antigenic or haptenic, and is a single compound or plurality of compounds which share at least one common epitopic or determinant site.

Sample Suspected of Containing Analyte

Any sample which is reasonably suspected of containing analyte can be analyzed by the method of the embodiments. Such samples can include human, animal or man-made samples. The sample can be prepared in any convenient medium which does not interfere with the assay. The sample may be an aqueous solution or a natural fluid, such as, urine, whole blood, serum, plasma, cerebral-spinal fluid, or saliva. In some embodiments, the sample is serum.

Measuring the Amount of Analyte

Quantitative, semiquantitative, and qualitative methods as well as all other methods for determining analyte are considered to be methods of measuring the amount of analyte. For example, a method which merely detects the presence or absence of analyte in a sample suspected of containing an analyte is considered to be included within the scope of the embodiments. Synonyms for the phrase "measuring the amount of analyte" which are contemplated within the scope of the embodiments include, but are not limited to, detecting, measuring, or determining analyte; detecting, measuring, or determining the presence of analyte; and detecting, or determining the amount of analyte.

Human Serum

"Human serum", as used herein, refers to the aqueous portion of human blood remaining after the fibrin and suspended material (such as cells) have been removed.

Immunoassay

As used herein, the terms "immunoassay" or "immunodiagnostic" refer to laboratory techniques or test systems that make use of the binding between an antigen or analyte and an antibody in order to identify and/or quantify at least one of the specific antigen or analyte or specific antibody in a biological sample.

As used here, the term "competitive immunoassay" refers to an experimental protocol in which a known amount of an identifiable antigen or analyte competes with another antigen or analyte for binding with an antibody. That is, a known antigen or analyte that binds with a known antibody is combined with a sample that is suspected of containing another antigen or analyte that also binds with the known antibody. This allows for the known antigen or analyte and another antigen or analyte to both compete for the binding site on the antibody. For example, a voriconazole derivative that binds with an anti-voriconazole antibody can be combined with a sample suspected of containing voriconazole, and the derivative and voriconazole compete for binding with the anti-voriconazole antibody. The competition for binding with the antibody can then be used to determine whether or not voriconazole is present in the sample, and can further be used to quantify the amount of voriconazole in the sample.

Member of a Specific Binding Pair

A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. In some embodiments, members of a specific binding pair are members of an immunological pair, such as antigen-antibody.

Ligand

A ligand is an organic compound for which a receptor naturally exists or can be prepared. For example, the analyte may be a ligand and embodiments of the present disclosure provide methods for determining the concentration of the ligand.

Receptor

A receptor is a compound or composition capable of recognizing a particular spatial and polar organization of a molecule. These organized areas of a molecule are referred to as epitopic or determinant sites. For example, receptors include, but are not limited to, antibodies and enzymes.

Linking Group

The term "linker" or "linking group" refers to a portion of a chemical structure that connects two or more substructures. A linking group has at least one uninterrupted chain of atoms extending between the substructures. The atoms of a linking group are themselves connected by chemical bonds. The number of atoms in a linking group is determined by counting the atoms other than hydrogen. Linking groups can include, but are not limited to, groups such as alkylene, heteroalkylene, cycloalkyl, heterocycloalkyl, aryl, heteroaryl, amino, as described herein.

Conjugate

A conjugate is a molecule that includes two or more substructures bound together, optionally through a linking group, to form a single structure. The binding can be made either by a direct connection (e.g., a chemical bond) between the subunits or by use of a linking group. For example, a conjugate may include a G6PDH enzyme or a label protein including alkaline phosphatase, β-galactosidase and horse radish peroxidase or a chemical label such as a fluorescent, luminescent or colorimetric molecule or microparticle attached to a hapten, sbp member, or analyte analog.

Conjugation

Conjugation is any process where two subunits are linked together to form a conjugate. The conjugation process can include one or more steps.

Derivative

As used herein, a "derivative" is a compound derived or obtained from another (e.g., a parent substance) and containing elements of the parent substance. Thus, in one embodiment, the term derivative refers to a chemical compound or molecule made from voriconazole by one or more chemical reactions. As such, a derivative can be a compound with a structure similar to that of voriconazole or based on voriconazole.

Hapten

Haptens are capable of binding specifically to corresponding antibodies, but usually do not themselves act as immunogens for preparation of the antibodies. Antibodies which recognize a hapten can be prepared against compounds that include the hapten linked to an immunogenic carrier.

Antibody

The term "anti-voriconazole antibody" refers to antibodies that are capable of specifically binding a voriconazole epitope of voriconazole, a voriconazole derivative, or a voriconazole conjugate. "Anti-voriconazole antibodies" include both polyclonal and monoclonal antibodies, as well as antigen-binding fragments thereof as defined herein. A "voriconazole epitope" refers to an epitope that is present in voriconazole and in a voriconazole derivative (e.g., a voriconazole conjugate).

The term "binds specifically" or "specifically binds" in the context of antibody binding, refers to high avidity and/or high affinity binding of an antibody to a specific antigen, e.g., to voriconazole. In specific binding under appropriate conditions, antibody binding to voriconazole is stronger than binding of the same antibody to any other epitope, particularly those which may be present in molecules in association with, or in the same sample, as the voriconazole to be detected, e.g., binds more strongly (e.g., higher affinity, higher avidity, or both) to voriconazole than to a non-voriconazole epitope so that by adjusting binding conditions the antibody binds almost exclusively to voriconazole or a voriconazole moiety as present in a compound of the present disclosure, and not to non-voriconazole moieties that may be present in the sample. Antibodies which bind specifically to voriconazole may be capable of binding other antigens at a weak, yet detectable, level (e.g., 10% or less of the binding shown to voriconazole). Such weak binding, or background binding, is readily discernible from the specific antibody binding to voriconazole, e.g., by use of appropriate controls. "Antibody activity" or "antibody binding activity" in the context of analyte binding assays generally refers to the ability of an antibody to bind a specific antigen or analyte in preference to other potential antigens or analytes via the antigen combining site located within a variable region of an immunoglobulin.

The term "antibody" includes a protein molecule having one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), epsilon (ε), and alpha (α) which encode the IgM, IgD, IgG, IgE, and IgA isotypes, respectively. "Antibody" as used herein is meant to include full length antibodies and antibody fragments, and may refer to a natural antibody from any organism, an engineered antibody, or an antibody generated recombinantly for experimental, therapeutic, or other purposes as further defined below. Thus, the term "antibody raised against a compound" includes a synthesized antibody or compound having the same structure as an antibody raised against the compound. The term "antibody" includes antibody fragments, as are known in the art, such as Fab, Fab', F(ab')$_2$, Fv, scFv, or other antigen-binding subsequences of antibodies, either produced by the modification of whole antibodies or those synthesized de novo using recombinant DNA technologies. The term "antibody" refers to both monoclonal and polyclonal antibodies. Antibodies can be antagonists, agonists, neutralizing, inhibitory, or stimulatory.

As used herein, the term "polyclonal antibody" refers to a heterogeneous mixture of antibodies with a wide range of specificities and affinities to a given antigen or epitope. Thus, the polyclonal antibody, which can also be referred to as polyclonal antibodies, can include a plurality of antibodies, each distinguishable from the others, that bind or otherwise interact with an antigen. The term "polyclonal" refers to antibodies originating from multiple progenitor cells. The different antibodies that comprise a polyclonal some antibody can be produced or generated by injecting an immunogen having an epitope into an animal and, after an appropriate time, collecting and optionally purifying the blood fraction containing the antibodies of interest. In producing antibodies, several parameters can be considered with respect to the final use for the polyclonal antibody. These parameters include the following: (1) the specificity of the antibody (i.e., the ability to distinguish between antigens); (2) the avidity of the antibody (i.e., the strength of binding an epitope); and (3) the titer of the antibody, which determines the optimal dilution of the antibody in the assay system.

As used herein, the term "monoclonal antibody" refers to an antibody that is isolated from a culture of normal antibody-producing cells and one unique progenitor cell. A monoclonal antibody can have a homogeneous binding constant. The monoclonal antibodies include an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies include hybrid and recombinant antibodies produced by splicing a variable (including hypervariable) domain of an anti-inhibitor antibody with a constant domain, or a light chain with a heavy chain, or a chain from one species with a chain from another species, or fusions with heterologous proteins, regardless of species of origin or immunoglobulin class or subclass designation, as well as antibody fragments, e.g., Fab, F(ab)2, and Fv1, that exhibit the desired biological activity. For example, the monoclonal antibodies may be made by the hybridoma method first described by Kohler & Milstein, *Nature*, 256: 495 (1975), or may be made by recombinant DNA methods (U.S. Pat. No. 4,816,567). The "monoclonal antibodies" may also be isolated from phage libraries generated using the techniques described in, e.g., McCafferty et al., *Nature*, 348:552-554 (1990).

Antigen

"Antigen", as used herein, refers to a compound that binds specifically to the variable region or binding site of an antibody. The term "antigen" and "immunogen" may in some cases be used interchangeably.

Epitope

The term "epitope" refers to a region of an antigen that interacts with an antibody molecule. An antigenic molecule can have one or more epitopes that can be recognized by the same or different antibodies. An epitope or epitopic moiety may comprise a unique chemical configuration of an antigen, hapten or a reactive ligand. The chemical configuration may be a linear sequence of chemical composition or even a spatial array of chemical groups in the chemical configuration. An epitope is the chemical configuration that associates directly with the binding site in the antibody molecule. The antibody and the chemical group, hapten or reacting ligand containing the epitope form the "specific binding pair."

Immunogen

As used herein, the terms "immunogen" and "immunogenic" are meant to refer to substances capable of producing or generating an immune response (e.g., antibody response) in an organism. An immunogen can also be antigen. In some embodiments, the immunogen has a high molecular weight (e.g., greater than 10,000). Thus, a variety of macromolecules such as proteins, lipoproteins, polysaccharides, nucleic acids and teichoic acids can be coupled to a hapten in order to form an immunogen in accordance with embodiments of the present disclosure.

As used herein, the term "immunogenicity" refers to the ability of a molecule to induce an immune response, which is determined both by the intrinsic chemical structure of the molecule and by whether or not the host animal can recognize the compound. Small changes in the structure of an antigen can greatly alter the immunogenicity of a compound and have been used extensively as a general procedure to increase the chances of raising an antibody, particularly against well-conserved antigens. For example, these modification techniques can alter regions of the immunogen to provide better sites for T-cell binding or expose new epitopes for B-cell binding.

Immunogenic Carrier

"Immunogenic carrier", "carrier," or "immunogenic moiety," as used herein, refers to any material that when combined with a hapten stimulates an in vitro or in vivo immune response. A hapten becomes an immunogenic moiety when coupled to a carrier and a part of the immunogen can induce an immune response and elicit the production of antibodies that can bind specifically with the hapten. Immunogenic carrier moieties include proteins, peptides (including polypeptides), glycoproteins, saccharides including complex polysaccharides, particles, nucleic acids, polynucleotides, and the like that are recognized as foreign and thereby elicit an immunologic response from the host.

Inhibitory Antibody

An inhibitory antibody is an antibody capable of inhibiting the activity of an enzyme or an enzyme-ligand conjugate upon binding an epitope present on the enzyme. Inhibitory antibodies are distinguished from anti-ligand antibodies capable of inhibiting the enzyme activity of enzyme-ligand conjugates upon binding to the ligand.

Accuracy

The term "accuracy" refers to the closeness of the agreement between the result of a measurand and a true value of the measurand. The measurand is the substance measured or analyzed, such as the analyte or the ligand entering the binding reaction with the receptor or antibody.

Specificity

The term "specificity" or "selectivity" refers to the preferential binding of a ligand to a receptor (e.g., antibody). Thus, specificity may refer, in one embodiment, to the degree that voriconazole is bound selectively by an antibody. One measure of the specificity of a receptor to a ligand is crossreactivity. Compounds that cross-react are referred to as "crossreactants." Crossreactants may occur as the result of the biotransformation of voriconazole by the human body to a metabolite, such as voriconazole being biotransformed into the N-oxide of voriconazole. Anti-voriconazole antibodies of the present disclosure include those that bind an epitope of voriconazole, but that do not detectably bind a metabolite of voriconazole, such as the N-oxide metabolite of voriconazole.

Sensitivity

The term "sensitivity" is used herein to describe a detection limit, e.g., the smallest amount of an analyte that results in a detectable signal that is distinguishable from a signal obtained in the absence of analyte.

Voriconazole Derivative

A "voriconazole derivative" as used in this disclosure refers to a compound sharing a core structure with voriconazole and that can compete with voriconazole for binding to an anti-voriconazole binding partner, such as an anti-voriconazole antibody.

Certain compounds disclosed herein in connection with embodiments can exist in unsolvated forms as well as solvated forms, including hydrated forms. In general, the solvated forms are equivalent to unsolvated forms and are encompassed within the reference to the compounds set out in the present disclosure. Certain compounds disclosed herein in connection with embodiments may exist in multiple crystalline or amorphous forms.

Reagent

A reagent is a substance or compound that is added to a system in order to bring about a chemical reaction, or added to see if a reaction occurs.

Isolated

As used herein, the term "isolated," when used in the context of an isolated compound, antibody, conjugate, etc., refers to a compound of interest (e.g., a compound as described herein, a conjugate as described herein, an antibody as described herein, etc.) that is in an environment different from that in which the compound naturally occurs. "Isolated" is meant to include compounds of interest (e.g., a compound as described herein, a conjugate as described herein, or an antibody as described herein) that are within samples that are substantially enriched for the compound of interest and/or in which the compound of interest is partially or substantially purified. As used herein, the term "substantially pure" refers to a compound of interest that is removed from its natural environment and is 60% or more free, 75% or more free, 90% or more free, 95% or more free, 98% or more free, or 99% or more free from other components with which it is naturally associated, and/or with which it may be associated during synthesis or production.

Certain compounds disclosed herein in connection with embodiments possess asymmetric carbon atoms (optical centers) or double bonds. The racemates, diastereomers, geometric isomers and individual isomers of these compounds are encompassed within the scope of the embodiments.

The compounds may be prepared as a single isomer (e.g., enantiomer, cis-trans, positional, diastereomer) or as a mixture of isomers. In one embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), Vogel's Encyclopedia of Practical Organic Chemistry, 5th ed., Longman Scientific and Technical Ltd., Essex, 1991, pp. 809-816; and Heller, Acc. Chem. Res. 23: 128 (1990).

Where substituent groups are specified by their conventional chemical formulae, written from left to right, they equally encompass the chemically identical substituents, which would result from writing the structure from right to left, e.g., —$CH_2O$— is intended to also recite —$OCH_2$—. Use of a single dash ("-") or double dash ("-" or "--") refers to a single covalent bond, while use of "=" refers to a double bond. The symbol,)$_2$ or $_2$(, when displayed with —S, indicates that the compound inside the parenthesis may be present as a dimer forming a disulfide bond. The dimer may be reduced to a monomer.

Acyl or Alkanoyl

The term "acyl" or "alkanoyl" by itself or in combination with another term, means, unless otherwise stated, a stable straight or branched chain, or cyclic hydrocarbon radical, or combinations thereof, having the stated number of carbon atoms and an acyl radical on at least one terminus of the alkane radical. The "acyl radical" is the group derived from a carboxylic acid by removing the —OH moiety therefrom.

Alkyl

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl.", where "heteroalkyl" refers to carbon chains having one or more substitutions at one or more carbon atoms of the hydrocarbon chain fragment. Alkyl groups that are limited to hydrocarbon groups are termed "homoalkyl". Certain alkyl groups include those containing between about one and about twenty five carbon atoms (e.g., methyl, ethyl, and the like).

Lower Alkyl

The term "lower alkyl" generally refers to a straight, branched, or cyclic hydrocarbon chain containing 8 or fewer carbon atoms, and can contain from 1 to 8, from 1 to 6, or from 1 to 4 carbon atoms. Certain "lower alkyl" groups include methyl, ethyl, n-propyl, isopropyl, n-butyl, sec-butyl, tert-butyl, n-pentyl, n-hexyl, n-heptyl and the like. "Lower alkyls" can be optionally substituted at one or more carbon atoms of the hydrocarbon chain.

Alkoxy, Alkylamino and Alkylthio

The terms "alkoxy," "alkylamino" and "alkylthio" (or thioalkoxy) are used to refer to those alkyl groups attached to the remainder of the molecule via an oxygen atom, an amino group, or a sulfur atom, respectively.

Heteroatom

By "heteroatom" is meant atoms other than a carbon which may be present in a carbon backbone or a linear, branched or cyclic compound. Certain heteroatoms include oxygen (O), nitrogen (N), sulfur (S), phosphorus (P) and silicon (Si). Heteroatoms can be present in their reduced forms, e.g., —OH, —NH, and —SH.

Heteroalkyl

The term "heteroalkyl," by itself or in combination with another term, means, unless otherwise stated, a straight or branched chain, or cyclic carbon-containing radical, or combinations thereof, having the stated number of carbon atoms and at least one heteroatom which can be a member selected from O, N, Si, P and S, where the nitrogen, phosphorous and sulfur atoms are optionally oxidized, and the nitrogen heteroatom is optionally quaternized. Normally heteroalkyl groups contain no more than two heteroatoms linked in sequence. The heteroatom(s) O, N, P, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Generally, up to two heteroatoms may be consecutive, such as, for example, —$CH_2$—NH—O$CH_3$ and $CH_2$—O—Si($CH_3$)$_3$.

Heteroalkylene

Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

Cycloalkyl and Heterocycloalkyl

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Aryl

The term "aryl" means, unless otherwise stated, a polyunsaturated, aromatic moiety that can be a single ring or multiple rings (usually from 1 to 3 rings), which are fused together or linked covalently. The term "heteroaryl" refers to aryl groups (or rings) that contain from one to four heteroatoms which are members selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Certain substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each can independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the embodiments includes more than one R group, for example, each of the R groups is independently selected, as are each R', R", R'" and R"" groups, when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of ordinary skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R'" and R"" can be independently selected from hydrogen, substituted or unsubstituted alkyl, substituted or unsubstituted heteroalkyl, substituted or unsubstituted aryl and substituted or unsubstituted heteroaryl. When a compound of the embodiments includes more than one R group, for example, each of the R groups is independently selected, as are each R', R", R'" and R"" groups, when more than one of these groups is present.

Amino and Amine Group

The term "amino" or "amine group" refers to the group —NR'R" (or N⁺RR'R") where R, R' and R" are independently selected from hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N⁺RR'R" and its biologically compatible anionic counterions.

Polypeptide

"Polypeptide" as used herein is meant to encompass a polyaminoacid of any length, and encompasses proteins, protein fragments and peptides. Polypeptides may be genetically encoded or synthetically produced. Polypeptides may also be modified, e.g., by post-translational and/or chemical modification(s).

Detectable Label

As used herein, a "detectable label" generally refers to an identifying tag that can provide for a detectable signal, e.g., luminescence (e.g., photoluminescence (e.g., fluorescence, phosphorescence), chemoluminescence (e.g., bioluminescence), microparticle aggregation or formation, radioactivity, immunodetection, enzymatic activity, and the like.

Detectably Labeled Antibody

By "detectably labeled antibody" is meant an antibody (which, as defined above, includes antigen-binding fragments, etc.) having an attached detectable label. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies to detect an antigen are well known in the art.

Antibody-Analyte Complex and Antibody-Antigen Complex

"Antibody-analyte complex", "antibody-antigen complex" generally refers to a complex that results following specific binding of an antibody and its antigen or analyte, e.g., between an anti-voriconazole antibody and voriconazole (or a voriconazole derivative, e.g., voriconazole conjugate).

Assessing

The term "assessing" includes any form of measurement, and includes determining the presence or absence if an element. The terms "assessing", "determining" (e.g., as in "determining the presence or absence of"), "measuring", "evaluating", and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

DETAILED DESCRIPTION

Before embodiments are described, it is to be understood that embodiments of the present disclosure are not limited to the particular embodiments described and, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the embodiments. The upper and lower limits of these smaller ranges may independently be included or excluded in the range, and each range where either, neither or both limits are included in the smaller ranges is also encompassed within the embodiments, subject to any specifically excluded limit in the stated range. Where the stated range includes one or both of the limits, ranges excluding either or both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can be used in the practice or testing of the embodiments, some methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It is also noted that as used herein and in the appended claims, the singular forms "a", "an", and "the" include plural referents unless the context clearly dictates otherwise. Thus, for example, reference to "a conjugate" includes a plurality of such conjugates and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present application is not entitled to antedate such publication by virtue of prior invention. Further, the dates of publication provided may be different from the actual publication dates which may need to be independently confirmed.

Immunoassays

Immunoassays (also known as immunodiagnostic test systems) measure a ligand or target analyte, the measurand (e.g., voriconazole), by using the selective binding properties of an antibody and a signal generating system that includes a signal generating moiety that is responsive or reactive to the presence of antibody due to the binding of the antibody with sbp member (e.g., hapten) conjugated to the signal generating moiety. Three classes of immunoassay are as follows: (1) antibody capture assays; (2) antigen capture assays; and (3) two-antibody sandwich assays. Additionally, it is contemplated that new immunoassays may be developed that are capable of employing the sbp members (e.g., hapten derivatives) and antibodies that form the specific binding pair of the embodiments of the present disclosure.

Homogeneous enzyme immunoassays use enzyme-sbp member conjugates whose enzyme activity can be modulated upon binding of the sbp partner. In one aspect, the embodiments provide enzyme-sbp member conjugates and antibodies for conducting assays that are useful in immunoassays. In certain embodiments, the immunoassay is a homogeneous immunoassay, where the term "homogeneous immunoassay", as used herein, refers to an assay method where the specific binding pair complex is typically in solution and not separated from unreacted reaction components, but instead the presence of the complex is detected by a property which at least one of the reactants acquires or loses as a result of being incorporated into the complex. Homogeneous assays include systems involving fluorochrome and fluorochrome quenching pairs on different reagents (U.S. Pat. Nos. 3,996,345; 4,161,515; 4,256,834 and 4,264,968); enzyme and enzyme inhibitor pairs on different reagents (U.S. Pat. Nos. 4,208,479 and 4,233,401); chromophore and chromophore modifier pairs on different reagents (U.S. Pat. No. 4,208,479); and latex agglutination assays (U.S. Pat. Nos. 3,088,875; 3,551,555; 4,205,954 and 4,351,824).

In certain embodiments, immunogens, such as immunogens that include a protein (e.g., an immunogenic carrier protein) conjugated to a voriconazole derivative (e.g., a voriconazole derivative according to a compound of formulae 1 or 2 herein), may be synthesized and used to prepare antibodies specific for voriconazole. The anti-voriconazole antibodies may be used in methods for detecting voriconazole in samples suspected of containing voriconazole.

In certain embodiments, label conjugates may be prepared and employed in the immunoassays described herein. The label conjugates may include a label conjugated to a voriconazole derivative (e.g., a voriconazole derivative according to a compound of formulae 1 or 2 herein). In certain embodiments, the immunoassays may facilitate the screening of samples for the presence of voriconazole.

The anti-voriconazole antibodies, either monoclonal or polyclonal, can be used in immunoassays for identifying the presence of voriconazole in a biological sample, such as blood, plasma, serum, urine, tissue, and the like. Immunoassays may facilitate identifying or determining pharmacokinetic and/or pharmacodynamic parameters for voriconazole in a patient or patient population. The anti-voriconazole antibodies can be used in immunodiagnostic assays configured for identifying the presence and optionally quantifying the amount of voriconazole in a sample. Additionally, the immunodiagnostic assays can use voriconazole derivatives in accordance with embodiments as described herein.

Voriconazole Derivatives

Voriconazole (1) and its major metabolite (2) are shown in FIG. 1. The major metabolic pathways in humans involve fluoropyrimidine N-oxidation, fluoropyrimidine hydroxylation, and methyl hydroxylation of voriconazole. In some cases, N-oxidation of voriconazole facilitates cleavage of the molecule, resulting in loss of the fluoropyrimidine moiety and subsequent conjugation with glucuronic acid. The major circulating metabolite in humans is the N-oxide of voriconazole (2).

In certain embodiments, voriconazole derivatives may be used to develop a specific assay for voriconazole. In some instances, voriconazole derivatives are haptens, where the fluoropyrimidine moiety of the chemical structure of voriconazole was retained and used to prepare immunogens and raise antibodies to voriconazole. In certain cases, attachment of the hapten (e.g., compounds VOR-5 and VOR-8) to a carrier protein was done through a site on voriconazole remote from the fluoropyrimidine moiety used to raise selective antibodies to voriconazole.

In certain embodiments, the derivatives of voriconazole described herein may be used in immunogens and label conjugates of the present disclosure. For instance, the immunogens and label conjugates may include a derivative of voriconazole modified at position 4 or 5 of the 2,4-difluorophenyl moiety of voriconazole.

Aspects of the present disclosure include a compound of Formula 1 shown below:

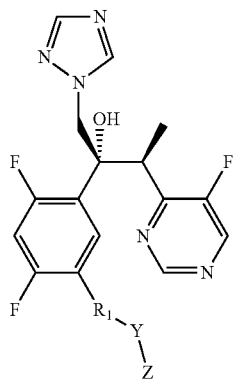

Formula 1 wherein
R$_1$ is —NH, —NHCO, —SH or —O;
Y is a linking group; and
Z is selected from the group consisting of hydrogen, —OH, —SH, —S-acyl; —O-lower alkyl, halogen, —NH$_2$, epoxy, maleimidyl, haloacetamide, carboxyl, activated carboxyl, an immunogenic carrier, a protein, and a label, and
salts thereof.

In certain embodiments, the activated carboxyl is an activated form of carboxyl including, but not limited to, hydroxysuccinimidyl, succinimidyl, carbonate, anhydride and imidate. In certain embodiments, the activated carboxyl is hydroxysuccinimidyl. In certain embodiments, the activated carboxyl is succinimidyl. In certain embodiments, the activated carboxyl is a carbonate. In certain embodiments, the activated carboxyl is an anhydride. In certain embodiments, the activated carboxyl is an imidate.

In certain embodiments, R$_1$ is —NH, —NHCO, —SH or —O. In certain embodiments, R$_1$ is —NH. In certain embodiments, R$_1$ is —NHCO. In certain embodiments, R$_1$ is —SH. In certain embodiments, R$_1$ is —O.

In certain embodiments, in Formula 1, Z is selected from the group consisting of hydrogen, —OH, —SH, —S-acyl; —O-lower alkyl, halogen, —NH$_2$, epoxy, maleimidyl, haloacetamide, carboxyl, and activated carboxyl. In certain embodiments, Z is selected from the group consisting of —OH, —SH, halogen, —NH$_2$, maleimidyl, carboxyl, and activated carboxyl. In certain embodiments, Z is carboxyl or activated carboxyl. In certain embodiments, Z is carboxyl. In certain embodiments, Z is activated carboxyl. In certain embodiments, Z is hydroxysuccinimidyl. In certain embodiments, Z is succinimidyl. In certain embodiments, Z is halogen, such as F, Cl, Br or I. In certain embodiments, Z is bromo. In certain embodiments, Z is —NH$_2$. In certain embodiments, Z is —SH.

In certain embodiments, in Formula 1, Z is an immunogenic carrier. Examples of immunogenetic carriers include proteins, peptides, glycoproteins, saccharides, particles, nucleic acids, and polynucleotides. In certain embodiments, Z is an immunogenic carrier is a protein. Examples of immunogenic carrier proteins include, but are not limited to, hemocyanins, globulins, and albumins. Examples of certain immunogenic carriers proteins include keyhole limpet hemocyanin (KLH), bovine serum albumin (BSA), or human serum albumin (HSA). In certain embodiments, Z is an immunogenic carrier protein is selected from BSA and KLH. In certain embodiments, the immunogenic carrier is a polysaccharide.

In certain embodiments, in Formula 1, Z is a label. Examples of labels for Z include, but are not limited to, isotopic labels and non-isotopic labels (e.g., signal generating moieties). Examples of isotopic labels include, but are not limited to, $^2$H, $^3$H, $^{13}$C, $^{14}$C, $^{15}$N, $^{32}$P, $^{33}$P, $^{35}$S, $^{125}$I, and the like. Examples of non-isotopic labels include signal generating moieties, such as, but not limited to, fluorophores and enzymes, which are described in further detail below.

In certain embodiments, the label is a fluorophore. Certain fluorophores include, but are not limited to, naphthalene derivatives (e.g., dansyl chloride), anthracene derivatives (e.g., N-hydroxysuccinimide ester of anthracene propionate), pyrene derivatives (e.g., N-hydroxysuccinimide ester of pyrene butyrate), fluorescein derivatives (e.g., fluorescein isothiocyanate), rhodamine derivatives (e.g., rhodamine isothiocyanate), phycoerythin, Texas Red, and the like.

In certain embodiments, the label is an enzyme. Certain enzymes include, but are not limited to, alkaline phosphatase, horseradish peroxidase, lysozyme, glucose-6-phosphate dehydrogenase (G6PDH), lactate dehydrogenase, β-galactosidase, and urease. Also, a genetically engineered fragment of an enzyme may be used, such as the donor and acceptor fragment of β-galactosidase utilized in CEDIA immunoassays. In certain embodiments, the enzyme is glucose-6-phosphate dehydrogenase (G6PDH), alkaline phosphatase, β-galactosidase, or horseradish peroxidase. In certain embodiments, the enzyme is glucose-6-phosphate dehydrogenase (G6PDH).

In certain embodiments, in Formula 1, R$_1$ is —NH, Y is a linking group, such as an alkylene linking group (e.g., a substituted or unsubstituted alkylene linking group), and Z is a carboxyl or activated carboxyl. For example, in certain instances, R$_1$ is —NH, Y is a linking group that includes 3 carbon atoms and one oxygen atom (e.g., an acyl group), and Z is a carboxyl. In certain embodiments, Formula 1 is a compound of the formula:

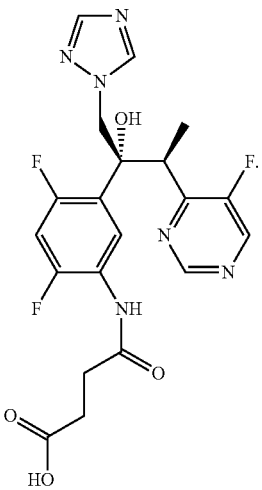 [SMILES: C[C@@H](c1ncncc1F)[C@](O)(Cn1cncn1)c1cc(NC(=O)CCC(=O)O)c(F)cc1F]

In certain embodiments, in Formula 1, R$_1$ is —NH, Y is a linking group, such as an alkylene linking group (e.g., a substituted or unsubstituted alkylene linking group), and Z is a carboxyl or activated carboxyl. For example, in certain instances, R$_1$ is —NH, Y is a linking group that includes 3 carbon atoms and one oxygen atom (e.g., an acyl group), and Z is an activated carboxyl, such as an activated carboxyl that includes a hydroxysuccinimidyl. In certain embodiments, Formula 1 is a compound of the formula:

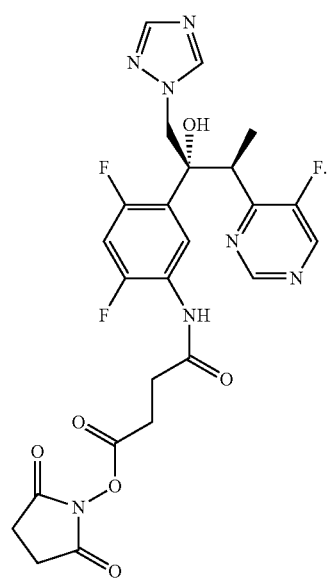 [SMILES: C[C@@H](c1ncncc1F)[C@](O)(Cn1cncn1)c1cc(NC(=O)CCC(=O)ON2C(=O)CCC2=O)c(F)cc1F]

Aspects of the present disclosure include a compound of Formula 2 shown below:

Formula 2

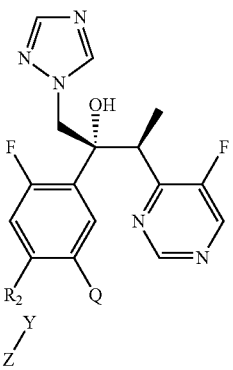

wherein
Q is —NO$_2$;
R$_2$ is —NH; —NHCO, —SH or —O;
Y is a linking group; and
Z is selected from the group consisting of hydrogen, —OH, —SH, —S-acyl; —O-lower alkyl, halogen, —NH$_2$, epoxy, maleimidyl, haloacetamide, carboxyl, activated carboxyl, an immunogenic carrier, a protein, and a label, and
salts thereof.

In certain embodiments, the activated carboxyl is an activated form of carboxyl including, but not limited to, hydroxysuccinimidyl, succinimidyl, carbonate, anhydride and imidate. In certain embodiments, the activated carboxyl is hydroxysuccinimidyl. In certain embodiments, the activated carboxyl is succinimidyl. In certain embodiments, the activated carboxyl is a carbonate. In certain embodiments, the activated carboxyl is an anhydride. In certain embodiments, the activated carboxyl is an imidate.

In certain embodiments, R$_2$ is —NH; —NHCO; —SH or —O. In certain embodiments, R$_2$ is —NH. In certain embodiments, R$_2$ is —NHCO. In certain embodiments, R$_2$ is —SH. In certain embodiments, R$_2$ is —O.

In certain embodiments, in Formula 2, Z is selected from the group consisting of hydrogen, —OH, —SH, —S-acyl; —O-lower alkyl, halogen, —NH$_2$, epoxy, maleimidyl, haloacetamide, carboxyl, and activated carboxyl. In certain embodiments, Z is selected from the group consisting of —OH, —SH, halogen, —NH$_2$, maleimidyl, carboxyl, and activated carboxyl. In certain embodiments, Z is carboxyl or activated carboxyl. In certain embodiments, Z is carboxyl. In certain embodiments, Z is activated carboxyl. In certain embodiments, Z is hydroxysuccinimidyl. In certain embodiments, Z is succinimidyl. In certain embodiments, Z is halogen, such as F, Cl, Br or I. In certain embodiments, Z is bromo. In certain embodiments, Z is —NH$_2$. In certain embodiments, Z is —SH.

In certain embodiments, in Formula 1, Z is an immunogenic carrier. Examples of immunogenetic carriers include proteins, peptides, glycoproteins, saccharides, particles, nucleic acids, and polynucleotides. In certain embodiments, Z is an immunogenic carrier is a protein. Examples of immunogenic carrier proteins include, but are not limited to, hemocyanins, globulins, and albumins. Examples of certain immunogenic carriers proteins include keyhole limpet hemocyanin (KLH), bovine serum albumin (BSA), or human serum albumin (HSA). In certain embodiments, Z is an immunogenic carrier protein is selected from BSA and KLH. In certain embodiments, the immunogenic carrier is a polysaccharide.

In certain embodiments, in Formula 1, Z is a label. Examples of labels for Z include, but are not limited to, isotopic labels and non-isotopic labels (e.g., signal generating moieties). Examples of isotopic labels include, but are not limited to, $^2$H, $^3$H, $^{13}$C, $^{14}$C, $^{15}$N, $^{32}$P, $^{33}$P, $^{35}$S, $^{125}$I, and the like. Examples of non-isotopic labels include signal generating moieties, such as, but not limited to, fluorophores and enzymes, which are described in further detail below.

In certain embodiments, the label is a fluorophore. Certain fluorophores include, but are not limited to, naphthalene derivatives (e.g., dansyl chloride), anthracene derivatives (e.g., N-hydroxysuccinimide ester of anthracene propionate), pyrene derivatives (e.g., N-hydroxysuccinimide ester of pyrene butyrate), fluorescein derivatives (e.g., fluorescein isothiocyanate), rhodamine derivatives (e.g., rhodamine isothiocyanate), phycoerythin, Texas Red, and the like.

In certain embodiments, the label is an enzyme. Certain enzymes include, but are not limited to, alkaline phosphatase, horseradish peroxidase, lysozyme, glucose-6-phosphate dehydrogenase (G6PDH), lactate dehydrogenase, β-galactosidase, and urease. Also, a genetically engineered fragment of an enzyme may be used, such as the donor and acceptor fragment of β-galactosidase utilized in CEDIA immunoassays. In certain embodiments, the enzyme is glucose-6-phosphate dehydrogenase (G6PDH), alkaline phosphatase, β-galactosidase, or horseradish peroxidase. In certain embodiments, the enzyme is glucose-6-phosphate dehydrogenase (G6PDH).

In certain embodiments, in Formula 2, R$_2$ is —NH, Y is a linking group, such as an alkylene linking group (e.g., a substituted or unsubstituted alkylene linking group), and Z is a carboxyl or activated carboxyl. For example, in certain instances, R$_2$ is —NH, Y is a linking group that includes 2 carbon atoms (e.g., an ethylene group), and Z is a carboxyl. In certain embodiments, Formula 2 is a compound of the formula:

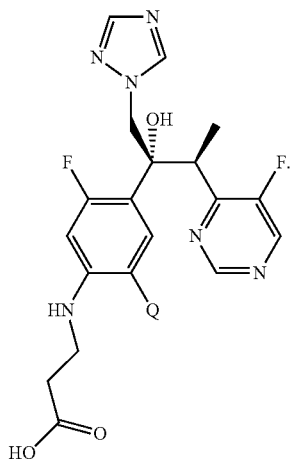

In certain embodiments, in Formula 2, R$_2$ is —NH, Y is a linking group, such as an alkylene linking group (e.g., a substituted or unsubstituted alkylene linking group), and Z is a carboxyl or activated carboxyl. For example, in certain instances, R$_2$ is —NH, Y is a linking group that includes 23 carbon atoms (e.g., an ethylene group), and Z is an activated carboxyl, such as an activated carboxyl that includes a hydroxysuccinimidyl. In certain embodiments, Formula 2 is a compound of the formula:

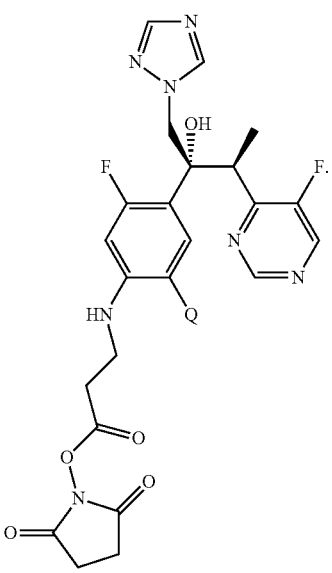

Linking Group

A linking group (also referred to herein as a linker) has at least 1 uninterrupted chain of atoms extending between the substructures, as depicted as Y in Formulae 1-2. The atoms of a linking group are themselves connected by chemical bonds. The number of atoms in a linking group is determined by counting the atoms other than hydrogen. In some embodiments, the linking group is a part of the compound of the embodiments. In some embodiments, the linker can provide a connection between, for example, the voriconazole derivative of Formula 1 and Z, or the voriconazole derivative of Formula 2 and Z.

The compounds may be connected to other species by bonding between a reactive functional group on the compound or a linker attached to the compound, and a reactive functional group of complementary reactivity on the other species. A linker may be, for example, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and combinations thereof. A linker may also include cyclic and/or aromatic groups as part of the chain or as a substitution on one of the atoms in the chain. In some embodiments, the linker may be used to provide an available site on a hapten for conjugating the hapten with, for example, a label, carrier, immunogenic carrier, or the like. The linker molecule may be used to connect (conjugate or couple) the ligand, hapten, epitope or epitopic moiety to its immunogenic carrier or signal generating moiety and to display the ligand, hapten, epitope or epitopic moiety for binding to a receptor or antibody. The length of the linker may be varied to accomplish the desired outcome in producing the immunogen or the signal generating system.

In certain embodiments of Formulae 1 and 2, the linking group includes 1 to 15 atoms and may include a chain of 2 to 8 atoms, each independently selected from the group consisting of carbon, oxygen, sulfur, nitrogen, halogen and phosphorous. Examples of linking groups include —(CH$_2$)$_n$—C(O)—, —C(O)(CH$_2$)$_n$—, —C(O)—(CH$_2$)$_n$—C(O)—, —C(O)(CH$_2$)$_n$—NHC(O)—, —C(O)(CH$_2$)$_n$—NHC(O)(CH$_2$)$_n$—, —(CH$_2$)$_n$SCH$_2$C(O)—, —(CH$_2$)$_n$—C(O)NH—(CH$_2$)$_n$—, —(CH$_2$)$_n$—NH—C(O)—, —(CH$_2$)$_n$—NH—C(O)—(CH$_2$)$_n$—, —C(O)—(CH$_2$)$_n$—C(O)O—, or —C(O)—(CH$_2$)$_n$—C(O)NH—, where n is an integer from 1 to 10, and including salts thereof.

In certain embodiments, the linking group is —C(O)—(CH$_2$)$_n$—C(O)NH—, where n is an integer from one to ten. In certain embodiments, the linking group is —C(O)—(CH$_2$)$_n$—C(O)NH—, where n is one or two. In certain embodiments, the linking group is —C(O)—(CH$_2$)$_n$—C(O)NH—, where n is two.

In certain embodiments, the linking group is —C(O)—(CH$_2$)$_n$—C(O)O—, where n is an integer from one to ten. In certain embodiments, the linking group is —C(O)—(CH$_2$)$_n$—C(O)O—, where n is one or two. In certain embodiments, the linking group is —C(O)—(CH$_2$)$_n$—C(O)O—, where n is two.

The number of heteroatoms in the linking group may range from 0 to 6, such as from 1 to 5 heteroatoms. The linking group may be aliphatic or aromatic. When heteroatoms are present, oxygen may be present as oxo or oxy, bonded to carbon, sulfur, nitrogen or phosphorous; nitrogen may be present as nitro, nitroso or amino, and may be bonded to carbon, oxygen, sulfur or phosphorous; sulfur may be present in analogous functional groups to oxygen; phosphorous may be bonded to carbon, sulfur, oxygen or nitrogen, such as phosphonate and phosphate mono- or diester. In certain embodiments, functionalities in forming a covalent bond between the linking group and the molecule to be conjugated include, but are not limited to, alkylamine, amidine, thioamide, ether, urea, thiourea, guanidine, azo, thioether, carboxylate, sulfonate, phosphate ester, amide and thioesters.

In certain embodiments, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities may be linked to amine groups, carboxyl groups, active olefins, alkylating agents, e.g., bromoacetyl. In certain embodiments, where an amine and carboxylic acid or its nitrogen derivative or phosphoric acid is linked, amides, amidines and phosphoramides are formed. In certain embodiments, where mercaptan and activated olefin are linked, thioethers are formed. In certain embodiments, where a mercaptan and an alkylating agent are linked, thioethers are formed. In certain embodiments, where aldehyde and an amine are linked under reducing conditions, an alkylamine is formed. In certain embodiments, where a carboxylic acid or phosphate acid and an alcohol are linked, esters are formed. Various linking agents are described in, for example, Cautrecasas, J. Biol. Chem. (1970) 245:3059.

Linking groups that link a carrier to a hapten can include modified or unmodified nucleotides, nucleosides, polymers, sugars and other carbohydrates, polyethers, such as for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. An example of an operative group and its linker is cholesterol-TEG-phosphoramidite, wherein the cholesterol is the operative group and the tetraethylene glycol and phosphate serve as linkers.

In some embodiments, the immunogenic carrier is a protein. Protein carriers can be highly soluble and include functional groups that may facilitate conjugation with a hapten molecule. In certain embodiments, the immunogenic carrier is selected from keyhole limpet hemocyanin (KLH), bovine serum albumin (BSA), and human serum albumin (HSA). KLH is a large oxygen-carrying protein of the marine keyhole limpet and exhibits increased immunogenicity when it is disassociated into subunits. BSA is a highly soluble protein containing numerous functional groups suitable for conjugation.

Derivatives

Derivatives of voriconazole in accordance with some embodiments can be used to compete for binding with a receptor including an antibody that recognizes both the derivative and voriconazole. A derivative can include an operative group coupled to voriconazole through a linker. Thus, the embodiments provide for voriconazole derivatives linked to, for example, an immunogenic carrier and/or a signal generating moiety as operative groups.

Signal Producing System

The signal producing system is utilized in assays for analytes and may have one or more components. In certain embodiments, the component is a mutant G6PDH. The signal producing system may be configured to generate a signal that relates to the presence or amount of analyte in a sample. The signal producing system may include reagents for producing a measurable signal. In some instances, the G6PDH or a label protein including alkaline phosphatase, β-galactosidase and horse radish peroxidase is conjugated to a sbp member analogous to the analyte.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, normally by measurement of electromagnetic radiation, such as a signal detectable by visual examination. In some cases, the signal producing system may include a chromophoric substrate and mutant G6PDH enzyme, where chromophoric substrates are enzymatically converted to dyes which absorb light in the ultraviolet or visible region.

Substantial Change in Enzyme Activity

A substantial change in activity of an enzyme is a change in enzyme activity sufficient to allow detection of an analyte when the enzyme is used as a label in an assay for the analyte. In some embodiments, the activity of the enzyme is reduced by 10-100%, such as reduced by 20-99%, including reduced by 30-95%.

Ancillary Materials

Various ancillary materials may be employed in an assay in accordance with the embodiments. For example, buffers may be present in the assay medium. In some instances, stabilizers for the assay medium and the assay components may be included. In certain embodiments, additional proteins may be included, such as albumins, or surfactants, such as non-ionic surfactants, binding enhancers, e.g., polyalkylene glycols, and the like.

Anti-Voriconazole Antibodies

As described above, the term "antibody" as used herein, refers to a specific binding partner of an analyte (e.g., voriconazole), and is meant to encompass whole antibodies as well as antigen-binding fragments thereof (such as, for example, F(ab')2, Fab', Fab and Fv), naturally occurring antibodies, hybrid antibodies, chimeric antibodies, single-chain antibodies, and antibody fragments that retain antigen binding specificity, and the like. Antibodies can be of any class (e.g., IgM, IgG, IgA, IgE; frequently IgG) and generated from any source (although usually non-human, such as a non-human mammal, such as a rabbit, mouse, rat, goat, etc.). Thus, "antibody" is meant to encompass not only intact immunoglobulin molecules, but also such fragments and derivatives of immunoglobulin molecules, and retaining the antibody activity of an intact immunoglobulin.

Antibodies may be derived from polyclonal compositions or monoclonal compositions. As noted above, "antibodies" is also meant to encompass single chain antibodies or scFvs, where such recombinantly produced antibody fragments retain the binding characteristics of the antibodies. Recombinantly produced antibody fragments within the meaning of "antibody" generally include at least the VH and VL domains of the subject antibodies, so as to retain the binding characteristics of the subject antibodies. These recombinantly produced antibody fragments may be readily prepared using any convenient methodology, such as the methodology disclosed in U.S. Pat. Nos. 5,851,829 and 5,965,371, the disclosures of which are herein incorporated by reference.

Anti-voriconazole antibodies include those that bind one or more voriconazole epitopes. Anti-voriconazole antibodies may bind one or more of unconjugated voriconazole, a voriconazole derivative, a voriconazole conjugate, or any combination thereof. The disclosure encompasses an antibody reactive to a common epitope present in voriconazole and compounds shown in Formulas 1 and 2. Such antibodies can thus bind a voriconazole epitope as present in voriconazole and a voriconazole moiety as present in a compound of any one of Formulae 1 to 2.

Producing Anti-Voriconazole Antibodies

Anti-voriconazole antibodies can be prepared by using an immunogenic voriconazole conjugate described herein and applying methods for antibody production. Examples of general techniques used in raising, purifying and modifying antibodies, and the design and execution of immunoassays are described in the Handbook of Experimental Immunology (D. M. Weir & C. C. Blackwell, eds.); Current Protocols in Immunology (J. E. Coligan et al., eds., 1991); David Wild, ed., The Immunoassay Handbook (Stockton Press N.Y., 1994); and R. Masseyeff, W. H. Albert, and N. A. Staines, eds., Methods of Immunological Analysis (Weinheim: VCH Verlags gesellschaft mbH, 1993).

Antibodies obtained using any of the disclosed techniques are screened or purified not only for their ability to react with voriconazole, but for a low cross-reactivity with potential interfering substances. "Cross-reactivity" may be determined in a quantitative immunoassay by establishing a standard curve using known dilutions of the target analyte, voriconazole. The standard curve is then used to calculate the apparent concentration of the interfering substance present in various known amounts in samples assayed under similar condition. The cross-reactivity can be calculated as the apparent concentration divided by the actual concentration multiplied by 100. A certain immunoassay for determining cross-reactivity is a homogeneous enzyme immunoassay using a wild type G6PDH as described in U.S. Pat. No. 3,817,837 or mutant G6PDH engineered to contain a cysteine per subunit as described in U.S. Pat. Nos. 6,033,890, 6,090,567 and 6,455,288. Furthermore, the cross-reactivity can be determined in the same type of immunoassay in which the antibody will ultimately be used.

In certain embodiments, anti-voriconazole antibodies of the present disclosure have a cross-reactivity of 25% or less, such as 20% or less, or 15% or less, or 10% or less, or 5% or less, or 3% or less, or 1% or less, with respect to binding of the anti-voriconazole antibody to other substances. For instance, anti-voriconazole antibodies of the present disclosure may have a cross-reactivity of 25% or less, such as 20% or less, or 15% or less, or 10% or less, or 5% or less, or 3% or less, or 1% or less, with respect to binding of the anti-voriconazole antibody to a voriconazole metabolite, such as voriconazole N-oxide. In some instances, anti-voriconazole antibodies of the present disclosure have a cross-reactivity of 25% or less, such as 20% or less, or 15% or less, or 10% or less, or 5% or less, or 3% or less, or 1% or less, with respect to binding of the anti-voriconazole antibody to other active agents, such as other azole drugs, including for example, fluconazole, itraconazole and posaconazole.

Producing Polyclonal Antibodies

Polyclonal antibodies that bind voriconazole may be raised by administration of an immunogenic voriconazole conjugate to an animal host, usually mixed with an adjuvant. Any animal host which produces antibodies can be used. The immunogen may be prepared for injection by rehydrating lyophilized immunogen to form a solution or suspension. Certain adjuvants are water-in-oil immersions, such as Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of anti-voriconazole antibody using a voriconazole-protein conjugate or other voriconazole conjugates in a standard immunoassay or precipitation reaction.

Methods for purifying specific antibodies having a desired binding specificity from a polyclonal antiserum are known in the art. An example of a method is affinity purification using a column of voriconazole conjugated to a solid phase. One manner of preparing a voriconazole column is to conjugate voriconazole or a voriconazole derivative to a protein other than the protein used in the immunogen, and then attach the conjugate to a commercially available activated resin, such as CNBr-activated SEPHAROSE™. The anti-voriconazole antibody is passed over the column, the column is washed, and the antibody is eluted with a mild denaturing buffer such as 0.1 M glycine, 0.2 M NaCl, pH 2.5.

Producing Monoclonal Antibodies

Anti-voriconazole monoclonal antibodies are prepared by a number of different techniques known in the art. For example, for hybridoma technology, techniques for producing monoclonal antibodies are described in Harrow E, Lane D., 1988, *Antibodies, A Laboratory Manual*, Cold Spring Harbor, N.Y.: Cold Spring Harbor Laboratory Press, and Methods in Enzymology, 73B:3 (1981). In certain embodiments, monoclonal antibodies are produced by immortalizing and cloning a splenocyte or other antibody-producing cell recovered from an animal that has been immunized against voriconazole as described earlier. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing may be performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using standard biochemical preparation techniques such as ammonium sulfate precipitation, ion exchange chromatography, and gel filtration chromatography.

Producing Fragments and Other Derivatives of Immunoglobulins

Fragments and other derivatives of immunoglobulins can be prepared by methods of standard protein chemistry, for example, subjecting the antibody to cleavage with a proteolytic enzyme such as pepsin, papain, or trypsin; and reducing disulfide bonds with such reagents as dithiothreitol. Genetically engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

Detectably Labeled Anti-Voriconazole Antibodies

The anti-voriconazole antibodies may also be labeled in order to facilitate detection. A variety of protein labeling schemes may be employed as desired depending on the intended use of the antibody, e.g. immunoassay.

Examples of labels include labels that permit both the direct and indirect measurement of the presence of the antibody. Examples of labels that permit direct measurement of the antibody include radiolabels, such as $^3$H or $^{125}$I fluorescers, dyes, microparticles, beads, chemiluminescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g., the antibody may be covalently bound to biotin and the enzyme conjugate to streptavidin. Examples of suitable enzymes for use in conjugates include horseradish peroxidase, alkaline phosphatase, malate dehydrogenase and the like.

Immunoassays

The present disclosure provides immunoassay methods for assessing the presence or absence of voriconazole in a sample of interest. Immunoassays of the present disclosure can be of a variety of formats. The immunoassays may be separation immunoassays (also known as heterogeneous immunoassays) or homogeneous immunoassays. Furthermore, the immunoassays may be qualitative or quantitative. Assays of this disclosure include both sandwich and competition assays. The immunoassays may embody assays that are neither sandwich nor competition assays, as in certain assays involving immunoprecipitation.

In general, the immunoassays of the present disclosure for detecting the presence or absence of voriconazole in a sample can be conducted by adding, to a reaction mixture, (i) a sample suspected of containing voriconazole and (ii) an anti-voriconazole antibody capable of forming a complex of voriconazole that may be present in the sample and the antibody; and detecting the presence or absence of the complex. The presence or absence of said complex is indicative of the presence or absence of voriconazole in said sample. Moreover, the amount of complex formed can be assessed to determine the concentration of voriconazole present in the sample (e.g., to provide an assessment of serum or tissue concentration of voriconazole in a subject from whom the sample was obtained). The presence and/or amount of complex can be assessed directly (e.g., by detecting bound antibody in the complex) or indirectly (e.g., by assessing activity of an enzyme in a voriconazole enzyme conjugate, where when the voriconazole enzyme conjugate is not bound to antibody, a detectable signal is generated, indicating that the anti-voriconazole antibody in the reaction mixture has been bound by voriconazole from the sample).

In general, the immunoassays of the disclosure entail combining the sample with an anti-voriconazole antibody under conditions that permit the formation of a stable complex between the analyte to be tested and the antibody.

Assays may be performed in solution or may use a solid (insoluble) support (e.g., polystyrene, nitrocellulose, or beads), using any standard methods (e.g., as described in Current Protocols in Immunology, Coligan et al., ed.; John Wiley & Sons, New York, 1992). Such methods include ELISAs (enzyme-linked immunosorbent assays), IRMAs (immunoradiometric assays), and RIAs (radioimmunoassays).

Where the assay is performed in solution, the test sample (and, optionally a control sample) may be incubated with an anti-voriconazole antibody for a time period sufficient to allow formation of analyte and affinity reagent complexes, for example, from 0.1 hrs to 24 hrs, or more. As previously noted, the anti-voriconazole antibody may include a detectable label (e.g., radionuclide, fluorescer, or enzyme). The sample may then be treated to separate the voriconazole-anti-voriconazole antibody complexes from excess, unreacted anti-voriconazole antibody (e.g., by addition of an anti-anti-voriconazole antibody (e.g., anti-immunoglobulin antiserum) followed by centrifugation to precipitate the complexes, or by binding to an affinity surface such as a second, unlabelled anti-voriconazole antibody fixed to a solid substrate such as Sepharose® or a plastic well). Detection of anti-voriconazole antibody bound to a voriconazole may be achieved in a variety of ways well known in the art. If necessary, a substrate for the detectable label may be added to the sample.

Where the assay uses a solid support, the support can have an anti-voriconazole antibody (or voriconazole conjugate) bound to a support surface. Binding of the assay reagent facilitates the stable, wash-resistant binding of voriconazole which may be present in the sample (or anti-voriconazole antibody that is not bound to voriconazole from the sample, and is present in the reaction mixture, as in a competitive binding assay) to the solid support via specific binding to the anti-voriconazole antibody. The insoluble supports may be any composition to which antibodies or suitable voriconazole conjugates can be bound, which can be separated from soluble material, and which is otherwise compatible with the overall method of detection of anti-voriconazole antibody a sample.

The surface of such supports may be solid or porous and of any convenient shape. Examples of suitable insoluble supports to which the anti-voriconazole antibody is bound include beads, e.g., magnetic beads, membranes and microtiter plates. These can be composed of glass, plastic (e.g., polystyrene), polysaccharides, nylon or nitrocellulose.

Assay reagents can include the anti-voriconazole antibodies as disclosed herein, as well as anti-anti-voriconazole antibodies, which may be optionally detectably labeled. After binding of an assay reagent to the support, the support may be treated with a blocking agent, which binds to the support in areas not occupied by the assay reagent Suitable blocking agents include non-interfering proteins such as bovine serum albumin, casein, gelatin, and the like. Alternatively, detergents at non-interfering concentrations, such as Tween, NP40, TX100, and the like may be used. Such blocking treatment may reduce nonspecific binding.

Qualitative and Quantitative Methods

Assays of this disclosure include both qualitative and quantitative assays. Typical quantitative methods involve mixing an analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise stated, the act of "measuring" or "determining" in this disclosure refers alternately to qualitative and quantitative determination.

Samples

Samples may be biological samples taken from subjects suspected of being administered voriconazole.

As used herein, a "biological sample" refers to a sample of tissue or fluid isolated from a subject, which in the context of the embodiments generally refers to samples suspected of containing voriconazole, which samples, after optional processing, can be analyzed in an in vitro assay.

Certain samples of interest include, but are not necessarily limited to, a "blood sample" (which as used herein is meant to include whole blood, plasma, serum, and the like), fecal matter, urine, tears, sweat saliva, milk, organs, biopsies, secretions of the intestinal and respiratory tracts, vitreous humor, and other fluids such as cerebrospinal fluid or fluids obtainable during autopsy. It should be noted that a "blood-derived sample" refers to a sample that is prepared from blood or a fraction thereof, e.g., plasma or serum. Respiratory secretions (e.g., samples obtained from fluids or tissue of nasal passages, lung, and the like). "Human serum", as used herein, refers to the aqueous portion of human blood remaining after the fibrin and suspended material (such as cells) have been removed.

Blood samples, such as serum samples, can be obtained by any suitable method. In one embodiment, a trough serum/plasma is used and the concentration range is 12-20 mg. Sweat samples can be obtained using, for example, a PharmChek® sweat patch from Sudormed. The Pharm-Chek® sweat patch includes a semi-occlusive dressing containing a medical grade cellulose blotter paper collection pad, covered by a thin layer of polyurethane and acrylate adhesives. At the end of the wear period, the pad is eluted with a suitable buffer, such as 2.5 mL of 0.2 M acetate buffer with methanol at pH 5.0 (25:75) or with acetonitrile. Furthermore, the biological samples may also be tissue samples, which are extracted into liquid medium for immunoassay. For example, hair samples can be tested by extracting into a liquid medium. The samples may be diluted or modified to facilitate the assay.

The samples may be experimental samples generated by any chemical or biological method. For example, the samples may be standards containing known concentrations of voriconazole or other substances used for assay calibration.

In some embodiments, the biological sample is diluted in a suitable solution prior to assaying. In general, a solution suitable for diluting a biological sample may include a buffer, such as phosphate buffered saline (PBS), and may include additional items, such as for example, a non-specific blocking agent, such as bovine serum albumin (BSA), a detergent, such as Triton-X-100, and the like.

Where desired, appropriate control samples for the assay include blood, serum, or urine collected from human subjects who have not received voriconazole (i.e., a negative control), or samples which contain a known, predetermined amount of a voriconazole analyte (i.e., a positive control). Alternatively, test results can be compared to detectable signal levels known to be associated with the presence or absence of voriconazole and/or correlated with an amount of voriconazole, e.g., a serum level of voriconazole.

The assays may optionally include use of a calibration standard. "Calibration standard", as used herein, refers to an aqueous medium containing voriconazole at a predetermined concentration. In certain embodiments, a series of these calibration standards are available at a series of predetermined concentrations. In certain embodiments, the calibration standard is stable at ambient temperature. In certain embodiments, the calibration standards are in a synthetic matrix. In certain embodiments, the calibration standards are in a non-synthetic matrix such as human serum.

In some embodiments, a suitable initial source for the human sample is a blood sample. As such, the sample employed in the subject assays may be a blood-derived sample. The blood derived sample may be derived form whole blood or a fraction thereof, e.g., serum, plasma, etc., where in some embodiments the sample is derived from blood allowed to clot and the serum separated and collected to be used to assay.

In embodiments in which the sample is a serum or serum derived sample, the sample is generally a fluid sample. Any convenient methodology for producing a fluid serum sample may be employed. In some embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Once the patient derived sample is obtained, the sample is assayed to determine the level of voriconazole analyte.

Immunoassay Reagents

Immunoassay reagents that find use alone or in combination in the assays described herein include anti-voriconazole antibodies, voriconazole conjugates, and voriconazole (e.g., as a control or in competitive binding assays). Immunoassay reagents can be provided in a buffered aqueous solution. Such solutions may include additional components such as surface active additives, organic solvents, defoamers, buffers, surfactants, and anti-microbial agents. Surface active additives are introduced to maintain hydrophobic or low-solubility compounds in solution, and stabilize components in the solution. Examples include bulking agents such as betalactoglobulin (BLG) or polyethyleneglycol (PEG); defoamers and surfactants such as Tween-20, Plurafac A38, Triton X-100, Pluronic 25R2, rabbit serum albumin (RSA), bovine serum albumin (BSA), and carbohydrates. Examples of organic solvents can include methanol and other alcohols. Various buffers may be used to maintain the pH of the solution during storage. Illustrative buffers include HEPES, borate, phosphate, carbonate, tris, barbital and the like. Anti-microbial agents also extend the storage life of the immunoassay reagent.

Anti-Voriconazole Antibodies

Immunoassays generally involve at least one anti-voriconazole antibody, which may be produced by the methods disclosed herein. In certain embodiments, the assays involve using an antibody raised against a voriconazole derivative-protein conjugate, particularly a low cross-reactivity with non-voriconazole molecules (i.e., molecules that are not voriconazole or contain a voriconazole moiety, such as present in a compound of the present disclosure, see, e.g., the compounds of Formulae 1-2) that may be present in a reaction mixture. Anti-voriconazole antibodies can be polyclonal or monoclonal antibodies capable of specifically binding voriconazole.

Depending upon the assay format, the anti-voriconazole antibody can be optionally detectably labeled, may be used in conjunction with a secondary antibody (i.e., an antibody that specifically binds an anti-voriconazole antibody) that may be detectably labeled. Certain detectable labels for antibodies are described herein.

Voriconazole Conjugates

Voriconazole conjugates find use as immunoassay reagents depending on the assay format. For example, a voriconazole conjugate can act as a competitive binding reagent in competitive binding assays, or can provide for a detectable signal when not bound by an anti-voriconazole antibody (e.g., where the voriconazole conjugate is a voriconazole G6PDH conjugate). Certain voriconazole conjugates useful as immunoassay reagents are described below.

Detectable Labels

A variety of detectable labels can be used in connection with the voriconazole conjugate assay reagents for use in the methods disclosed herein. Such detectable labels can be isotopic labels. In other embodiments, the detectable labels are non-isotopic signal-generating moieties, such as fluorophores and enzymes. Certain detectable labels are described below. It will be apparent that while the detectable labels are described below in the context of their use in voriconazole conjugates, they can also be adapted for use with anti-voriconazole antibodies.

Fluorophores

"Fluorophore" as used herein refers to a moiety that itself fluoresces, can be made to fluoresce, or can provide for quenching of fluorescence of a fluorophore of a FRET pair (e.g., as in a FRET pair). In principle, any fluorophore can be used in the assays of the embodiments. In general, the fluorophore is selected so as to be compatible for use in the assay format desired, and selected so as to be relatively insensitive to the assay conditions, e.g., pH, polarity, temperature and ionic strength.

Certain fluorophores can be characterized as having the following characteristics: (a) a fluorescence lifetime of greater than 15 nsec; (b) an excitation wavelength of greater than 350 nm; (c) a Stokes shift (a shift to lower wave-length of the emission relative to absorption) of greater than 20 nm; (d) for homogeneous assays described below, fluorescence lifetime should vary with binding status; and (e) the absorptivity and quantum yield of the fluorophore should be high. The longer lifetime is advantageous because it may facilitate measurement and may be more easily distinguishable from the Raleigh scattering (background). Excitation wavelengths greater than 350 nm may reduce background interference because most fluorescent substances responsible for background fluorescence in biological samples are excited below 350 nm. A greater Stokes shift may also allow for less background interference.

The fluorophores generally have a functional group available for conjugation either directly or indirectly to a voriconazole intermediate to generate a voriconazole conjugate having the attached fluorophore.

Fluorophores for use in heterogeneous assays can be relatively insensitive to binding status. In contrast, fluorophores for use in homogeneous assay can be sensitive to binding status, i.e., the fluorescence lifetime must be alterable by binding so that bound and free forms can be distinguished.

Examples of fluorophores include, but are not limited to, naphthalene derivatives (e.g., dansyl chloride), anthracene derivatives (e.g., N-hydroxysuccinimide ester of anthracene propionate), pyrene derivatives (e.g., N-hydroxysuccinimide ester of pyrene butyrate), fluorescein derivatives (e.g., fluorescein isothiocyanate), rhodamine derivatives (e.g., rhodamine isothiocyanate), phycoerythin, Texas Red, and the like.

Enzymes

As discussed herein, the voriconazole conjugate may be a label conjugate (e.g., a voriconazole derivative of formulae 1 or 2 herein conjugated to a detectable label). In some instances, the detectable label is a non-isotopic label, such as a signal-generating moiety. In certain embodiments, the signal-generating moiety is an enzyme. In some cases, the enzyme facilitates a reaction that produces an enzymatic reaction product. In certain instances, the enzymatic reaction product produces a detectable signal. As such, in certain embodiments, methods of the present disclosure include immunoassays where detecting the presence of voriconazole in a sample includes determining the presence of an enzymatic reaction product of the label conjugate.

The enzyme can be selected so as to be stable to provide for desirable shelf-life, e.g., stable when stored for a period of three months or more, or six months or more, at temperatures which are convenient to store in the laboratory, such as −20° C., or above. The enzyme can be selected so as to have a satisfactory turnover rate at or near the pH optimum for binding to the antibody, which may be at about pH 6-10, such as pH 6 to 8. A product of the enzymatic reaction facilitated by the enzyme can be either formed or destroyed as a result of the enzyme reaction, and can provide an enzymatic reaction product which absorbs light in the ultraviolet region or the visible region, such as a range of 250-750 nm, including 300-600 nm. The enzyme may also have a substrate (including cofactors), which has a molecular weight of 300 or more, or 500 or more. The enzyme which is employed or other enzymes, with like activity, may not be present in the sample to be measured, or can be easily removed or deactivated prior to the addition of the assay reagents. Also, the enzyme can be selected so as to avoid the impact of any naturally occurring inhibitors for the enzyme that may be present in samples to be assayed or as some other component of the reaction mixture.

Although enzymes of 600,000 molecular weight or more can be employed, in some embodiments relatively low molecular weight enzymes will be employed, such as from 10,000 to 300,000 molecular weight, including from 10,000 to 150,000 molecular weight, or from 10,000 to 100,000 molecular weight. Where an enzyme has a plurality of subunits the molecular weight ranges refer to the enzyme and not to the subunits.

It may be desirable to select an enzyme that is susceptible to detectable labeling. In some instances, the enzyme can be detectably labeled using appropriate detectable labels exemplified herein.

Certain enzymes include, but are not limited to, alkaline phosphatase, horseradish peroxidase, lysozyme, glucose-6-phosphate dehydrogenase, lactate dehydrogenase, β-galactosidase, and urease. Also, a genetically engineered fragment of an enzyme may be used, such as the donor and acceptor fragment of β-galactosidase utilized in CEDIA immunoassays (see, e.g., Henderson D R et al. Clin Chem. 32(9):1637-1641 (1986)); U.S. Pat. No. 4,708,929. These and other enzymes which can be used are discussed in Eva Engvall in Enzyme Immunoassay ELISA and EMIT in Methods in Enzymology, 70:419-439 (1980) and in U.S. Pat. No. 4,857,453.

In certain embodiments, the enzyme is glucose-6-phosphate dehydrogenase (G6PDH) and is attached to a voriconazole derivative, thus forming a voriconazole-reactive partner conjugate. An anti-voriconazole antibody used in conjunction with such voriconazole conjugates can be selected so as to specifically bind the voriconazole epitope presented by the voriconazole enzyme conjugate, and thus affect activity of the voriconazole-enzyme conjugate.

For assays employing voriconazole-enzyme conjugates, as a certain protein conjugate, in which a voriconazole derivative is labeled with an enzyme, the voriconazole derivative can be attached to the enzyme by any suitable method. In certain embodiments, the chemistry described herein for formation of immunogenic protein conjugates of voriconazole derivatives is also used to prepare the enzyme conjugate. In this way, the voriconazole moiety presented to the antibody can mirror the voriconazole epitope to which the antibody specifically binds.

The selection procedure is exemplified using a voriconazole-reactive partner conjugate that includes G6PDH as the reactive partner and a voriconazole derivative as the hapten. The first step in selecting an antibody involves testing the magnitude of antibody inhibition of a voriconazole-reactive partner conjugate. In this step, antibodies which significantly inhibit the enzyme activity of G6PDH are selected. Antibodies which perform well in the first test are then subjected to a second test. Here, the antibody is first incubated with voriconazole. Next, the voriconazole-reactive partner conjugate is added. A certain antibody preferentially binds to voriconazole instead of the voriconazole-reactive partner conjugate. The reduction in binding to the voriconazole-reactive partner conjugate would be visible as an increase G6PDH activity.

Detection

Via Fluorescence

When a fluorescently labeled analyte (i.e., voriconazole antigen or antibody) is employed, the fluorescence emitted is proportional (either directly or inversely) to the amount of analyte. The amount of fluorescence is determined by the amplitude of the fluorescence decay curve for the fluorescent species. This amplitude parameter is directly proportional to the amount of fluorescent species and accordingly to the analyte.

In general, spectroscopic measurement of fluorescence is accomplished by: (a) exciting the fluorophore with a pulse of light; (b) detecting and storing an image of the excitation pulse and an image of all the fluorescence (the fluorescent transient) induced by the excitation pulse; (c) digitizing the image; (d) calculating the true fluorescent transient from the digitized data; and (e) determining the amplitude of the fluorescent transient as an indication of the amount of fluorescent species.

According to the method, substantially all of the fluorescence emitted by the fluorescent species reaching the detector as a function of time from the instant of excitation is measured. As a consequence, the signal being detected may be a superimposition of several component signals (for example, background and one analyte specific signal). As mentioned, the individual contributions to the overall fluorescence reaching the detector may be distinguished based on the different fluorescence decay rates (lifetimes) of signal components. In order to quantitate the magnitude of each contribution, the detected signal data may be processed to obtain the amplitude of each component. The amplitude of each component signal may be proportional to the concentration of the fluorescent species.

Via Enzyme

Detection of the amount of product produced by the voriconazole-reactive partner conjugate of the embodiments can be accomplished by several methods, such as, but not limited to, colorimetry, fluorescence, and spectrophotometry. These methods of detection are discussed in "Analytical Biochemistry" by David Holme, Addison-Wesley, 1998, which is incorporated herein by reference.

Solid Supports

The voriconazole conjugates and/or the anti-voriconazole antibodies to be used as reagents in an assay can be insolubilized by attachment to a solid phase. This can be, for example, a wall of a vessel containing the reagent, to a particulate, or to a large molecular weight carrier that can be kept in suspension but is removable by physicochemical means, such as centrifugation or microfiltration. The attachment need not be covalent, but is at least of sufficient permanence to withstand any separation techniques (including washes) that are part of the assay procedure. Certain particulate materials include agarose, polystyrene, cellulose, polyacrylamide, latex particles, magnetic particles, and fixed red cells. Examples of commercially available matrices include Sepharose® (Pharmacia), Poros® resins (Roche Molecular Biochemicals), Actigel Superflow™ resins (Sterogene Bioseparations Inc.), and Dynabeads™ (Dynal Inc.). The choice is not critical, and will generally depend on such features as stability, capacity, accessibility of the coupled antibody, flow rate (or the ability to disperse the resin in the reaction mixture), and ease of separation.

Assay Formats

As noted above, immunoassays for detection of voriconazole can be of a variety of formats, In general, the immunoassays involve combining one or more immunoassay reagents (e.g., at least an anti-voriconazole antibody) with a test sample (i.e., a sample suspected of containing voriconazole) in a reaction mixture. "Reaction mixture" generally refers to the combination of a sample suspected of containing voriconazole and one or more immunoassay reagents as exemplified in the present disclosure to facilitate detection of the presence or absence of voriconazole in the sample, where the detection may be qualitative or quantitative. The reaction mixture is usually an aqueous solution, although the immunoassay reagent(s) may be in solution or immobilized on a support (e.g., a substrate such as a bead). The reaction mixture can include other components compatible with the immunoassay, e.g., buffers, and the like.

Immunoassays usually are classified in one of several ways. For example, immunoassays can be classified according to the mode of detection used, i.e., enzyme immunoassays, radio immunoassays, fluorescence polarization immunoassays, chemiluminescence immunoassays, turbidimetric assays, etc. Another grouping method is according to the assay procedure used, i.e., competitive assay formats, sandwich-type assay formats as well as assays based on precipitation or agglutination principles. In certain instances, a further distinction is made depending on whether washing steps are included in the procedure (so-called heterogeneous assays) or whether reaction and detection are performed without a washing step (so-called homogeneous assays). Certain assays are described in more detail below.

Homogeneous and Heterogeneous Immunoassays

Immunoassays may be described as heterogeneous or homogeneous. "Homogeneous immunoassay", as used herein, refers to an assay method where the complex is not separated from unreacted reaction components, but instead the presence of the complex is detected by a property which at least one of the reactants acquires or loses as a result of being incorporated into the complex. Homogeneous assays include systems involving fluorochrome and fluorochrome quenching pairs on different reagents; enzyme and enzyme inhibitor pairs on different reagents; chromophore and chromophore modifier pairs on different reagents; and latex agglutination assays.

A certain homogeneous assay is the quantitative homogeneous enzyme immunoassay in which a voriconazole moiety is conjugated to an active enzyme. The conjugation is arranged so that the binding of an anti-voriconazole antibody to the derivative affects enzymatic activity in a qualitative or quantitative fashion. If a sample containing voriconazole is premixed with the antibody, the antibody may complex with the voriconazole and thus be prevented from binding to the enzyme conjugate. In this way, the activity of the enzyme can be correlated with the amount of voriconazole present in the sample.

G6PDH is a certain enzyme useful in such assays. In some embodiments, the G6PDH is a variant of a naturally-occurring G6PDH in which one or more lysine residues are deleted or substituted, or one or more cysteine residues are introduced. For example, *Leuconostoc mesenteroides* G6PDH are dimeric enzymes that have the ability to catalyze the oxidation of D-glucose-6-phosphate to D-glucono-delta-lactone-6-phosphate by utilizing either $NAD^+$ or $NADP^+$. This property of using NAD differentiates these enzymes from human G6PDH, which utilizes only NADP effectively, and allows *L. mesenteroides*-specific G6PDH activity to be measured in the presence of human G6PDH, as for example in human samples. Two certain genera of bacteria from which to select G6PDH are *Leuconostoc* and *Zymomonas*. Within these genera *L. mesenteroides, L. citreum, L. lactis, L. dextranicum*, and *Z. mobilis* are of interest, where *L. mesenteroides, L. citreum*, and *L. lactis* are specific examples.

Another example of a homogeneous assay system is the cloned enzyme donor immunoassay.

In a separation-based or "heterogeneous" assay, the detecting of a complex of an anti-voriconazole antibody and an analyte involves a process wherein the complex formed is physically separated from either unreacted analyte, unreacted antibody, or both.

In a heterogeneous immunoassay, a complex of an anti-voriconazole antibody and an analyte may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled derivative or antibody to facilitate detection or quantitation of the complex. Suitable labels include radioisotopes such as $^{125}I$, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

Sandwich and Competition Assays

Assays of this disclosure include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with a derivative of the analyte for binding to another reagent, such as an antibody. An example of a competition assay using EMIT® is described in U.S. Pat. No. 3,817,837.

In some embodiments, the immunoassay further includes adding a voriconazole conjugate that has a voriconazole moiety and a detectable label to the sample. The presence or absence of voriconazole in the sample can be detected by detecting the datable label. The detectable label may include an enzyme and the detecting may be by assaying activity of the enzyme. In certain embodiments, the enzyme is a dehydrogenase, such as G6PDH.

Lateral Flow Chromatography

The compounds and methods of the embodiments also encompass the use of these materials in lateral flow chromatography technologies. Lateral flow chromatography involves a membrane strip which includes a detection device, such as a non-isotopic signal generating moiety, for voriconazole. A sample from a patient may then be applied to the membrane strip. The sample may interact with the detection device, producing a result. The results can signify several things, including the absence of the voriconazole in the sample, the presence of the voriconazole in the sample, or the concentration of the voriconazole in the sample.

Certain embodiments provide a method of qualitatively determining the presence or absence of a voriconazole in a sample, through the use of lateral flow chromatography. In certain embodiments, the basic design of the qualitative lateral flow device is as follows: 1) The sample pad is where the sample is applied. The sample pad is treated with chemicals such as buffers or salts, which, when redissolved, optimize the chemistry of the sample for reaction with the conjugate, test, and control reagents; 2) Conjugate release pad is typically a polyester or glass fiber material that is treated with a conjugate reagent such as an antibody colloidal gold conjugate. A typical process for treating a conjugate pad is to use impregnation followed by drying. In use, the liquid sample added to the test will redissolve the conjugate so that it will flow into the membrane; 3) The membrane substrate is usually made of nitrocellulose or a similar material whereby antibody capture components are immobilized; 4) A wicking pad is used in tests where blood plasma must be separated from whole blood. An impregnation process is usually used to treat this pad with reagents intended to condition the sample and promote cell separation; 5) The absorbent pad acts as a reservoir for collecting fluids that have flowed through the device; and 6) The above layers and membrane system are laminated onto a plastic backing with adhesive material which serves as a structural member.

Certain embodiments provide a method of qualitatively determining the presence of a voriconazole in a sample, through the use of lateral flow chromatography. In these embodiments, the membrane strip includes a sample pad, which is a conjugate release pad (CRP) that has an antibody that is specific for the voriconazole. This antibody may be conjugated to a non-isotopic signal-generating moiety, such as a colloidal gold particle. Other detection moieties useful in a lateral flow chromatography environment include dyes, colored latex particles, fluorescently labeled latex particles, non-isotopic signal generating moieties, etc. In some instances, the membrane strip further includes a capture line, in which the voriconazole derivative antigen is immobilized on the strip. In some embodiments, this immobilization is through covalent attachment to the membrane strip, optionally through a linker. In other embodiments, the immobilization is through non-covalent attachment to the membrane strip. In still other embodiments, the immobile voriconazole derivative in the capture line is attached to a reactive partner, such as an immunogenic carrier like BSA.

Sample from a patient may be applied to the sample pad, where it can combine with the antibody in the CRP, thus forming a solution. This solution may then migrate chromatographically by capillary action across the membrane. When the voriconazole is present in the sample, a voriconazole-antibody complex is formed, which migrates across the membrane by capillary action. When the solution reaches the capture line, the voriconazole-antibody complex will compete with the immobile voriconazole for the limited binding sites of the antibody. When a sufficient concentration of voriconazole is present in the sample, it will fill the limited antibody binding sites. This will prevent the formation of a colored antibody-immobile voriconazole complex in the capture line. Therefore, absence of color in the capture line indicates the presence of voriconazole in the sample.

In the absence of voriconazole in the sample, a colored antibody-immobile voriconazole complex will form once the solution reaches the capture line of the membrane strip. The formation of this complex in the capture line is evidence of the absence of voriconazole therapeutic in the sample.

Certain embodiments provide a method of quantitatively determining the amount of a voriconazole in a sample, through the use of lateral flow chromatography. This technology is further described in U.S. Pat. Nos. 4,391,904; 4,435,504; 4,959,324; 5,264,180; 5,340,539; and 5,416,000, the disclosures of which are herein incorporated by reference. In some embodiments, the antibody is immobilized along the entire length of the membrane strip. In general, if the membrane strip is made from paper, the antibody may be covalently bound to the membrane strip. If the membrane strip is made from nitrocellulose, then the antibody can be non-covalently attached to the membrane strip through, for example, hydrophobic and electrostatic interactions. The membrane strip may include a CRP which comprises the voriconazole attached to a detector moiety. In certain embodiments, the detector moiety is an enzyme, such as horseradish peroxidase (HRP).

In certain embodiments, sample from a patient is applied to the membrane strip, where it can combine with the voriconazole/detector molecule in the CRP, thus forming a solution. This solution may then be allowed to migrate chromatographically by capillary action across the membrane. When the voriconazole is present in the sample, both the sample voriconazole and the voriconazole/detector molecule compete for the limited binding sites of the antibody. When a sufficient concentration of voriconazole is present in the sample, it will fill the limited antibody binding sites. This will force the voriconazole/detector molecule to continue to migrate in the membrane strip. The shorter the distance of migration of the voriconazole/detector molecule in the membrane strip, the lower the concentration of voriconazole in the sample, and vice versa. When the voriconazole/detector molecule includes an enzyme, the length of migration of the voriconazole/detector molecule can be detected by applying an enzyme substrate to the membrane strip. Detection of the product of the enzyme reaction may then be utilized to determine the concentration of the voriconazole in the sample. In certain embodiments, the enzyme's color producing substrate such as a modified N,N-dimethylaniline is immobilized to the membrane strip and 3-methyl-2-benzothiazolinone hydrazone is passively applied to the membrane, thus alleviating the need for a separate reagent to visualize the color producing reaction.

Fluorescence Polarization Immunoassay for Voriconazole

Fluorescence polarization immunoassay (FPIA) technology is based upon competitive binding between an antigen/drug in a sample and a known concentration of labeled antigen/drug. FPIA technology is described in, for example, U.S. Pat. Nos. 4,593,089, 4,492,762, 4,668,640, and 4,751,190, the disclosures of which are incorporated herein by reference. The FPIA reagents, systems, and equipment can be used with anti-voriconazole antibodies which are also anti-voriconazole analog antibodies.

The FPIA technology can be used to identify the presence of voriconazole and can be used in assays that quantify the amount of voriconazole in a sample. In part, the rotational properties of molecules in solution allow for the degree of polarization to be directly proportional to the size of the molecule. Accordingly, polarization increases as molecular size increases. That is, when linearly polarized light is used to excite a fluorescent-labeled or other luminescent-labeled voriconazole or derivative thereof, which is small and rotates rapidly in solution, the emitted light is significantly depolarized. When the fluorescent-labeled voriconazole or derivative interacts with or is bound to an antibody, the rotation is slowed and the emitted light is highly polarized. This is because the antibody significantly and measurably increases the size of the complex. Also, increasing the amount of unlabeled voriconazole in the sample can result in decreased binding of the fluorescent-labeled voriconazole or derivative by the anti-voriconazole antibody, and thereby decrease the polarization of light emitted from sample. The quantitative relationship between polarization and concentration of the unlabeled voriconazole in the sample can be established by measuring the polarization values of calibrations with known concentrations of voriconazole. Thus, FPIA can be used to identify the presence and concentration of voriconazole in a sample.

In some embodiments, the assay involves an FPIA assay system. An example of components of the FPIA system can include the following: i) monoclonal or polyclonal anti-voriconazole antibodies capable of specifically binding to voriconazole and a voriconazole derivative; ii) a sample suspected of containing the voriconazole; and iii) voriconazole derivative labeled with a fluorescent moiety, such as fluorescein. Alternatively, the system can be provided as a kit exclusive of the sample. Additionally, the system can include various buffer compositions, voriconazole concentration gradient compositions or a stock composition of voriconazole, and the like.

Homogeneous Microparticle Immunoassay for Voriconazole

Homogeneous microparticles immunoassay ("HMI") technology, which can be referred to as immunoturbidimetric assays, is based on the agglutination of particles and compounds in solution. When particles and/or chemical compounds agglutinate, particle sizes can increase and increase the turbidity of a solution. Accordingly, anti-voriconazole antibodies can be used with microparticles and voriconazole derivatives in order to assess the presence, and optionally the amount, of voriconazole in a sample. HMI technologies can be advantageous because the immunoassays can be performed on blood, blood hemolysate, serum, plasma, tissue, and/or other samples. HMI assays can be configured to be performed with voriconazole and/or a voriconazole derivative loaded onto a microparticle, or with an anti-voriconazole antibody loaded onto a microparticle. HMI or immunoturbidimetric assays are well known in the art for measuring agglutination of substances in a sample.

Immunoturbidimetric assay technologies are described in, e.g., U.S. Pat. Nos. 5,571,728, 4,847,209, 6,514,770, and 6,248,597, the disclosures of which are incorporated herein by reference. Such assays involve light attenuation, nephelometric, or turbidimetric methods. The formation of an agglutinated compound AB from voriconazole (A) and anti-voriconazole antibody microparticle binding partner (B) can be measured by the change which occurs in the scattering or absorption of the incident light directed into the sample. Alternatively, the anti-voriconazole antibody (A) can bind with a voriconazole or derivative loaded microparticle. When suspendable particles having an immobilized binding partner are used, there is an enhancement of the effects, which makes it possible to determine lower voriconazole concentrations. These homogeneous methods can be carried out quickly and simply, and may facilitate the automation of sample analyses as described in more detail below.

Cloned Enzyme Donor Immunoassays for Voriconazole

Cloned enzyme donor Immunoassays ("CEDIA®", Roche Diagnostics), as are based upon the competition of voriconazole in the biological sample with a voriconazole conjugate containing an inactive genetically engineered enzyme-donor ("ED") fragment such as from β-D-galactoside galactohydrolase or β-galactosidase ("β-gal") from *E. coli*, for binding to an antibody capable of binding voriconazole. If voriconazole is present in the sample it binds to the antibody, leaving the ED portion of the ED-derivative conjugate free to restore enzyme activity of β-D-galactoside galactohydrolase or B gal in the reaction mixture so as to be capable of association with enzyme acceptor ("EA") fragments. The active enzyme comprised of the ED and EA is then capable of producing a quantifiable reaction product when exposed to an appropriate substrate. An example of a substrate is chlorophenol red-β-D-galactopyranoside ("CPRG"), which can be cleaved by the active enzyme into galactose and CPR, wherein CPR is measured by absorbency at about wavelength 570 nm. If voriconazole is not present in the sample, the antibody binds to the ED-derivative conjugate, thereby inhibiting association of the ED fragments with the EA fragments and inhibiting restoration of enzyme activity. The amount of reaction product and resultant absorbance change are proportional to the amount of voriconazole in the sample.

Chemiluminescent Heterogeneous Immunoassays for Voriconazole

A competitive assay using chemiluminescent microparticle immunoassay ("CMIA") technology can also be used to assess whether or not voriconazole is present in a sample. Various types of CMIA technologies may be used for determining the presence and/or amount of a chemical entity in a sample. CMIA assays can include the use of anti-voriconazole antibodies, which are capable of binding to voriconazole and its derivatives, which are coupled to particles, such as magnetic particles or particles suitable for separation by filtration, sedimentation, and/or other means. Additionally, a tracer, which can include a voriconazole derivative linked to a suitable chemiluminescent moiety, can be used to compete with free voriconazole in the patient's sample for the limited amount of anti-voriconazole antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free drug in the patient's sample and concentration is determined by constructing a standard curve using known values of the drug.

Other Immunoassays for Voriconazole

The voriconazole derivatives, conjugates, antibodies, immunogens, and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the voriconazole derivatives, conjugates, antibodies, immunogens and/or tracers, such assays can also be modified as is well known in the art. As such, various modifications of steps or acts for performing such immunoassays can be made within the scope of the embodiments.

Kits

The present disclosure also provides kits that find use in practicing the subject methods, as described above, such as a method for performing an assay for the determination of voriconazole in a sample. The kits of the embodiments can include an anti-voriconazole antibody in a container, and may include a voriconazole conjugate (e.g., for use in a competitive binding assay, for use in an enzyme-based assay, and the like). For example, an immunoassay kit may include at least one antibody for an immunogen of an analyte, e.g., voriconazole, and at least one enzyme conjugate that corresponds to that analyte, e.g., an enzyme conjugate of a derivative of vorionazole. In certain embodiments, a kit for an assay for the analyte voriconazole includes in packaged combination: (i) an antibody raised against the compound of any of the above formulas 1 and 2; and (ii) a conjugate of a derivative of the analyte.

Reagents and buffers used in the assays can be packaged separately or in combination into kit form to facilitate distribution. The reagents may be provided in suitable containers, and may be provided in a package along with written instructions relating to assay procedures (e.g., instructions for an assay for detecting voriconazole in a sample). For example, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention.

Various ancillary materials may be employed in an assay in accordance with the embodiments. In certain embodiments, buffers and/or stabilizers are present in the kit components. In certain embodiments, the kits include indicator solutions or indicator "dipsticks", blotters, culture media, cuvettes, and the like. In certain embodiments, the kits include indicator cartridges (where a kit component is bound to a solid support) for use in an automated detector. In certain embodiments, additional proteins, such as albumin, or surfactants, particularly non-ionic surfactants, may be included. In certain embodiments, the kits include an instruction manual that teaches a method of the embodiments and/or describes the use of the components of the kit. For example, embodiments of the kit may include: (a) an antibody raised against a voriconazole derivative; (b) ancillary reagents for determining the compound (as described herein); and (c) a labeled conjugate of a compound of the above formulas 1 and 2.

Embodiments of the present disclosure also include a kit for conveniently determining the presence or the absence of voriconazole in a sample. The kit may include an anti-voriconazole antibody and a voriconazole calibration standard. The voriconazole calibration standard may include calibration and control standards useful in performing the assay. The kits can also optionally include a conjugate that includes a voriconazole moiety and a detectable label. In certain embodiments, a detectable label of the conjugate is an enzyme. In some embodiments, the enzyme is glucose-6-phosphate dehydrogenase (G6PDH). In some embodiments, the G6PDH is a variant of a naturally-occurring G6PDH in which one or more lysine residues are deleted or substituted, or one or more cysteine residues are introduced.

Utility

The compounds, methods and kits of the present disclosure find use in routine therapeutic drug monitoring of voriconazole by immunoassays. In certain embodiments, these immunoassays provide simple automated tests adapted to standard laboratory equipment with a quick turn-around time. As described herein, in order to provide such immunoassays, antibodies specific to voriconazole are produced. The derivatives and immunogens are designed to impart through the corresponding antibodies produced specific reactivity to voriconazole.

General Synthetic Schemes

Figure 3:
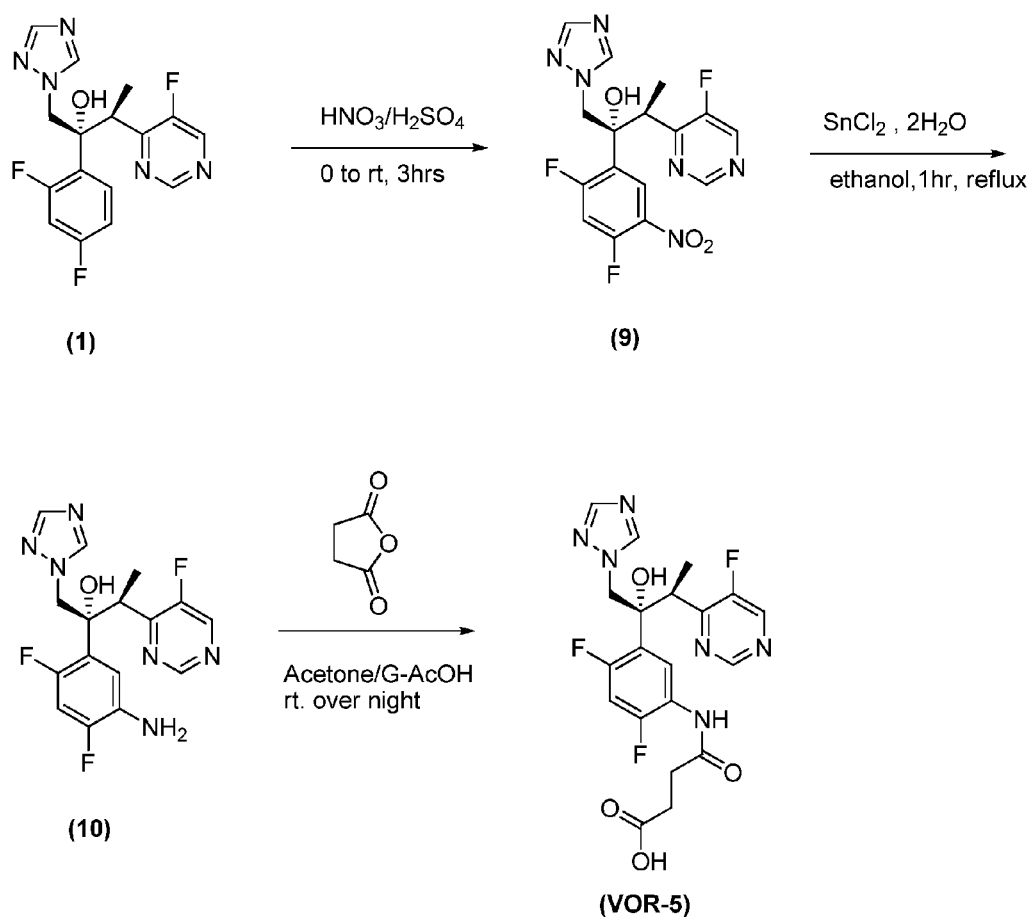
FIG. 3 shows a synthetic scheme for the synthesis of voriconazole hapten (VOR-5) according to embodiments of the present disclosure.

In certain embodiments, voriconazole derivatives substituted at the 5-position of the 2,4-difluorophenyl moiety of voriconazole may be produced. As shown in FIG. 3, compound (VOR-5) may be synthesized by aromatic nitration of voriconazole (1) to produce compound (9). For example, voriconazole (1) may be treated with a mixture of nitric acid and sulfuric acid to form 5-nitro voriconazole analog (9). The 5-nitro voriconazole analog (9) may then be isolated and the nitro group may be reduced to form the resulting 5-amino voriconazole analog (10). The amine may be acylated with succinic anhydride to produce the 5-succinylamino derivative of voriconazole, compound (VOR-5). In some cases, the 5-succinylamino derivative of voriconazole, compound (VOR-5), may be purified before proceeding to the next step.

Figure 4:
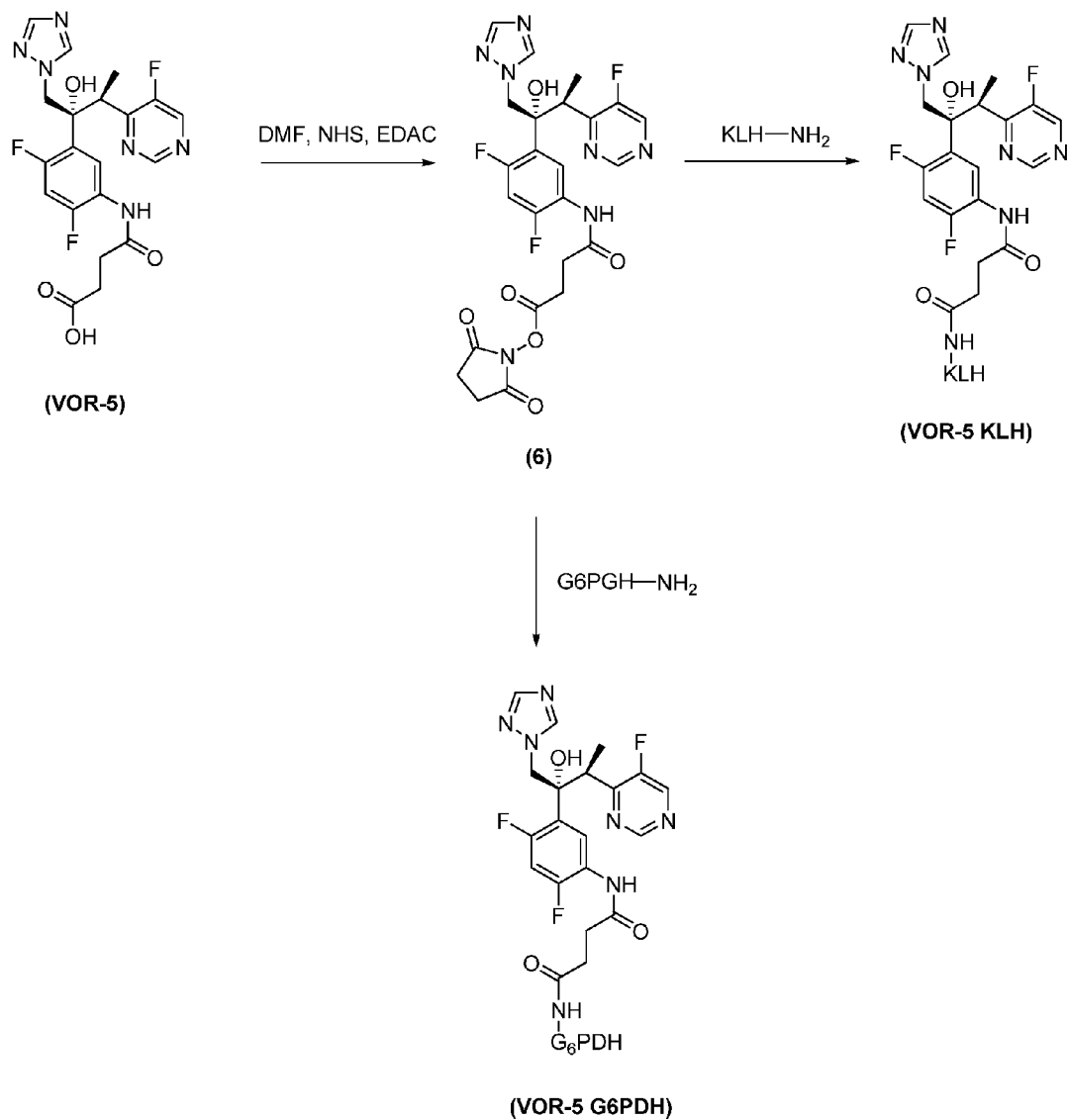
FIG. 4 shows a synthetic scheme for the synthesis of a Keyhole Limpet Hemocyanin (KLH) immunogen (VOR-5 KLH) and a Glucose-6-Phosphate Dehydrogenase (G6PDH) conjugate (8) from an N-hydroxy succinimide (NHS) ester voriconazole hapten (6) substituted at the 5-position, according to embodiments of the present disclosure.

As shown in FIG. 4, the acid group of compound (VOR-5) may be converted to an N-hydroxysuccinimide ester (compound (6)) and linked through the nitrogen to a protein to produce compound (VOR-5 KLH), or a label to produce compound (VOR-5 G6PDH), respectively. For example, a purified derivative of voriconazole, compound (VOR-5), may be reacted with NHS (N-hydroxysuccinimide) in the presence of a carbodiimide to prepare an amine-reactive ester of carboxylate group for chemical labeling. The resulting semi-stable NHS ester may then be reacted with primary amines (—NH$_2$) present in proteins or the label enzyme to form amide crosslinks.

Figure 5:
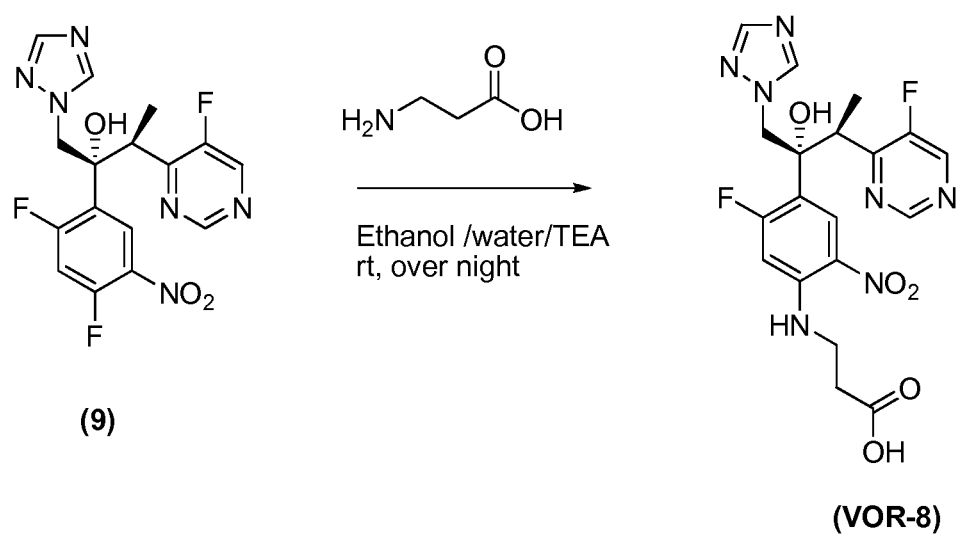
FIG. 5 shows a synthetic scheme for the synthesis of a voriconazole hapten (VOR-8), according to embodiments of the present disclosure.

In certain embodiments, voriconazole derivatives substituted at the 4-position of the 2,4-difluorophenyl moiety of voriconazole may be produced. As shown in FIG. 5, compound (VOR-8) may be prepared by reacting compound (9) with β-alanine to produce compound (VOR-8). For example, compound (9) and β-alanine may be added to a mixture of ethanol and water. Triethylamine may be added and reacted overnight resulting in compound (VOR-8). Compound (VOR-8) may then be purified.

Figure 6:
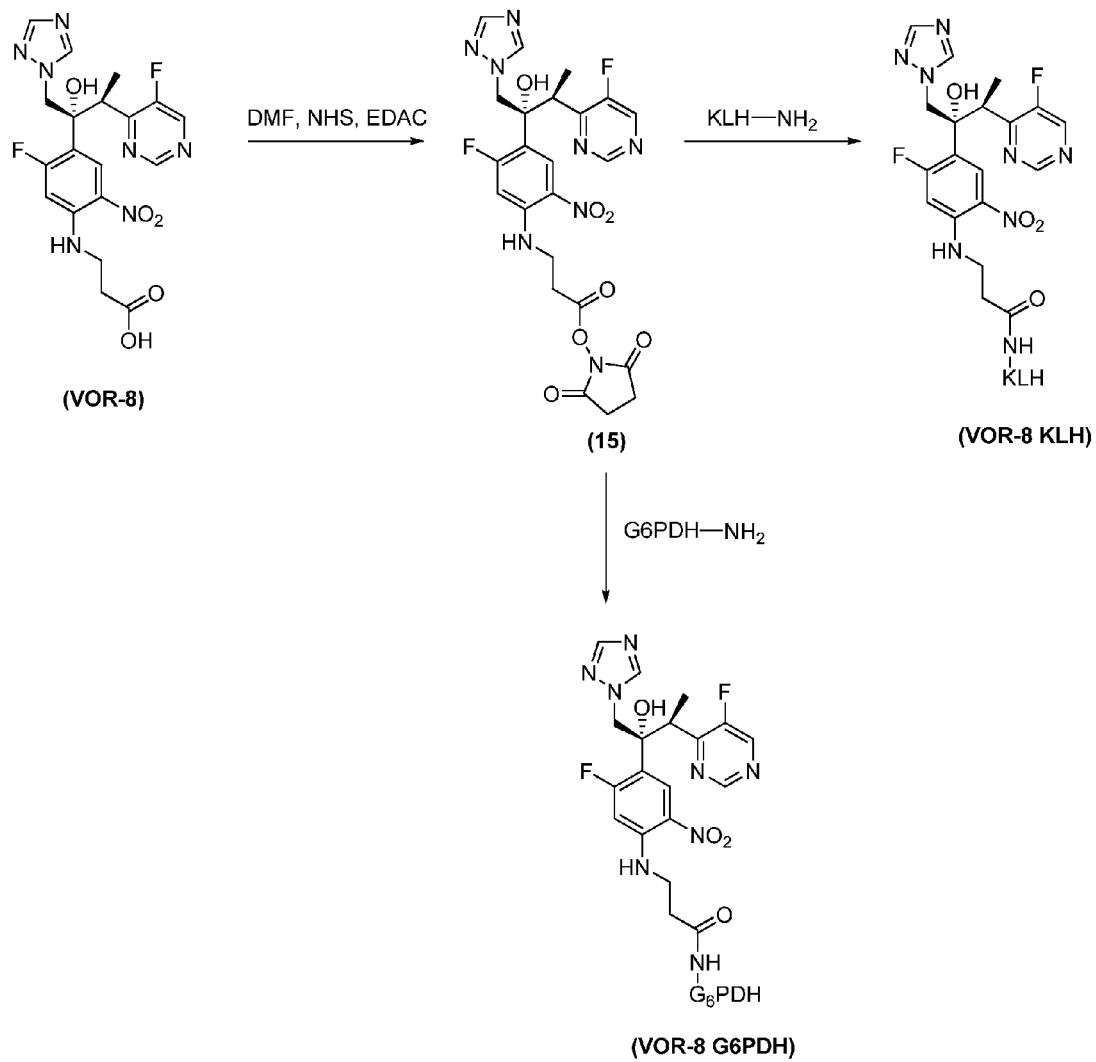
FIG. 6 shows a synthetic scheme for the synthesis of a KLH immunogen (VOR-8 KLH) and a G6PDH conjugate (VOR-8 G6PDH) from an NHS ester voriconazole hapten (15) substituted at the 4-position, according to embodiments of the present disclosure.

As shown in FIG. 6, the carboxylic acid group of compound (VOR-8) may be converted to an N-hydroxysuccinimide ester (compound (15)) and linked through the nitrogen to a protein to produce compound (VOR-8 KLH), or a label to produce compound (VOR-8 G6PDH), respectively. For example, a purified derivative of voriconazole, compound (VOR-8), may be reacted with NHS (N-hydroxysuccinimide) in the presence of a carbodiimide to prepare an amine-reactive ester of carboxylate group for chemical labeling. The resulting semi-stable NHS ester may then be reacted with primary amines (—NH$_2$) present in proteins or the label enzyme to form amide crosslinks.

Immunogens prepared with voriconazole derivatives (VOR-5) and (VOR-8) provide for antibodies that react with voriconazole. Antibodies that are specific to voriconazole may be utilized for different immunoassay formats.

EXAMPLES

The following examples are offered by way of illustration and not by way of limitation. It should be apparent that the present disclosure can include additional embodiments not illustrated by example. Additionally, many of the examples have been performed with experimental protocols well known in the art using the voriconazole derivatives, antigens, immunogens, and anti-voriconazole derivative antibodies prepared in accordance with the present disclosure.

Synthesis

Synthesis of Novel Voriconazole Haptens and Immunogens of the Present Invention

Voriconazole (1) was treated with a mixture of nitric acid and sulfuric acid to form 5-nitro voriconazole analog (9). The 5-nitro voriconazole analog (9) was then isolated and reduced to form the resulting 5-amino voriconazole analog (10), which was acylated with succinic anhydride to form the 5-succinylamino derivative of voriconazole (VOR-5). The 5-succinylamino derivative of voriconazole (VOR-5) was then purified. See FIG. 3.

The purified 5-succinylamino derivative of voriconazole (VOR-5) was reacted with NHS (N-hydroxysuccinimide) in the presence of a carbodiimide such as ethyl(dimethylaminopropyl) carbodiimide (EDAC) to prepare amine-reactive esters of carboxylate group for chemical labeling. The resulting semi-stable NHS ester of the 5-succinylamino derivative of voriconazole (12) was then reacted with primary amines (—NH$_2$) present in proteins or the label enzyme to form amide crosslinks.

In addition, the 5-nitro voriconazole analog (9) was reacted with β-alanine to form compound (VOR-8). The purified derivative of voriconazole (VOR-8) was reacted with NHS (N-hydroxysuccinimide) in the presence of a carbodiimide such as ethyl(dimethylaminopropyl) carbodiimide (EDAC) to prepare amine-reactive esters of carboxylate group for chemical labeling. The resulting semi-stable NHS ester of the derivative of voriconazole (19) was then reacted with primary amines (—NH$_2$) present in proteins or the label enzyme to form amide crosslinks.

All the prepared haptens (VOR-5 and VOR-8) were used for preparation of KLH immunogens (VOR-5 KLH and VOR-8 KLH) and G6PDH conjugates (VOR-5 G6PDH and VOR-8 G6PDH). Immunogens (VOR-5 KLH and VOR-8 KLH) were used for elicitation of specific antibodies to voriconazole (1). In an enzyme-based assay format, antibodies showed good modulation with voriconazole free drug. The immunogens (VOR-5 KLH and VOR-8 KLH) were used to raise antibodies, which were used in an enzyme-based voriconazole immunoassay.

Preparation of Antibodies

The following method may be employed to prepare polyclonal antibodies using the immunogens in Formulas 1 and 2. Antiserum containing antibodies was obtained by immunization of an animal, such as rabbits and sheep, with an appropriate immunogen and obtaining antisera from the blood of the immunized animal after an appropriate waiting period. Reviews of the preparation of antibodies are provided by Parker, Radioimmunoassay of Biologically Active Compounds, Prentice-Hall (Englewood Cliffs, N.J., U.S., 1976), Butler, *J. Immunol. Meth.* 7: 1 24 (1975); Broughton and Strong, Clin. *Chem.* 22: 726 732 (1976); and Playfair, et al., *Br. Med. Bull.* 30: 24 31 (1974).

The following procedure may be employed to prepare monoclonal antibodies for the immunogens of Formulas 1 and 2. Monoclonal antibodies are produced according to the standard techniques of Kohler and Milstein, *Nature* 265:495 497, 1975. Reviews of monoclonal antibody techniques are found in Lymphocyte Hybridomas, ed. Melchers, et al. Springer-Verlag (New York 1978), *Nature* 266: 495 (1977), *Science* 208: 692 (1980), and *Methods of Enzymology* 73 (Part B): 3 46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device. Various conventional ways exist for isolation and purification of the monoclonal antibodies from other proteins and other contaminants (see Kohler and Milstein, supra).

Figure 7A:
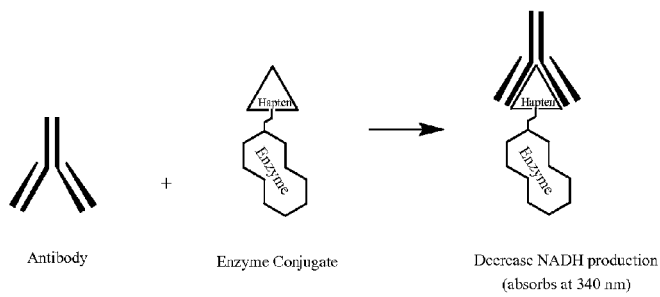
FIGS. 7a and 7b are flow diagrams illustrating embodiments of a method for performing an immunodiagnostic assay for voriconazole, according to embodiments of the present disclosure. The rate of increasing absorbance at 340 nm due to the conversion of NAD+ (Nicotinamide Adenine Dinucleotide reduced) to NADH (Nicotinamide Adenine Dinucleotide oxidized) is related to the concentration of voriconazole in the sample by a mathematical function. The enzyme reaction is catalyzed by the voriconazole-enzyme conjugate.
Figure 7B:
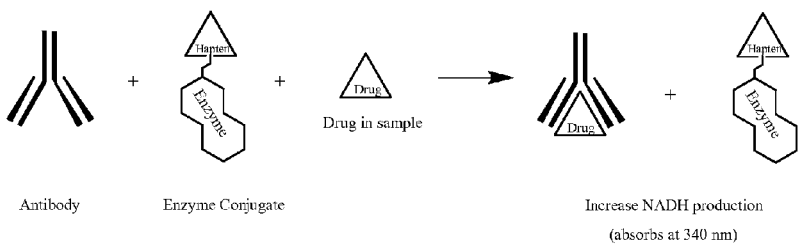

Antibodies can be purified by techniques such as chromatography, e.g., DEAE chromatography, ABx chromatography, and the like, filtration, and so forth. Antibodies may be screened using any of several techniques, for example using an assay format as illustrated in FIG. 7, and considering such properties as specificity, conjugate inhibition, curve size and cross-reactivity.

Experimental Details

Analytical thin layer chromatography (TLC) was performed on Analtech Uniplate Silica Gel GF (0.25 mm) glass-backed plates using the specified solvent. The spots on TLC were visualized by ultraviolet light (short and/or long wave) and/or iodine vapors. Flash chromatography was carried out on Whatman silica gel 60 Å (230 400 mesh). All chemicals were obtained from Sigma, Aldrich, Fluka or Lancaster and used as received. $^1$H-NMR and C-NMR spectra were recorded on a Bruker Ultrashiel™-400 (400 MHz) spectrometer. Chemical shifts were reported in parts per million (ppm, δ and related to tetramethylsilane or with deuterated solvent as the internal reference. NMR abbreviations used are s (singlet), d (doublet), and m (multiplet).

Example 1

Preparation of Compound (9)

Fuming $HNO_3$ (600 µl) was added to cold concentrated $H_2SO_4$ (3 mL). Voriconazole (1) (1 g, 2.5 mmol)) was added in one portion. The reaction mixture was allowed to warm up slowly to room temperature while stifling for 3 hrs. The reaction mixture was then added to a cold saturated solution of sodium bicarbonate (60 mL) and pH was adjusted to 7 by adding more solid sodium bicarbonate. This solution was extracted with ethyl acetate (3×30 mL) and washed with brine (30 mL), dried over $MgSO_4$, filtered and concentrated to give 1.1 g crude product. This material was triturated with ethyl acetate (2×15 mL) to give 630 mg clean desired product as a yellow solid. To the wash solvent was added hexane (20 mL) and let stand at 4° C. over night to give 220 mg more desired product. A total of 850 mg compound (9) was obtained (77%). Compound (9) had the m/e=396 (M+1). See FIG. 3.

Example 2

Preparation of Compound (10)

Compound (9) (580 mg, 1.47 mmol) was taken into ethanol (15 mL) and $SnCl_2$ (1.4 g, 6.2 mmol) was added. The mixture was refluxed for one hour. Solvent was evaporated, water (20 mL) was added and the pH was adjusted to 7 by adding 1N NaOH. The mixture was extracted with ethyl acetate (2×50 mL) and washed with brine. The organic layer was dried over $MgSO_4$ and concentrated to give 514 mg compound (10) as a yellow solid. This material was purified on silica gel using methanol/dichloromethane (5/95) to give 450 mg clean compound (10) (84%). Compound (10) had the m/e=365 (M+1). See FIG. 3.

Example 3

Preparation of Compound (VOR-5)

Compound (10) (320 mg, 0.87 mmol) and succinic anhydride were dissolved in glacial acetic acid (1.5 mL) and stirred for 2 hours at room temperature. Water (25 mL) was added to the reaction mixture and extracted twice with ethyl acetate (2×25 mL). The organic layer was washed with brine (10 mL), dried over $MgSO_4$, filtered and concentrated to give 380 mg crude yellow solid. The crude product was taken in to hot ethyl acetate (20 mL) and triturated. The mixture was cooled to room temperature and decanted. The yellow solid was washed with ethyl acetate (10 mL) and dried under vacuum to give 187 mg clean compound (VOR-5) (46%). Compound (VOR-5) had the m/e=465 (M+1). See FIG. 3.

Example 4

Preparation of Compound (VOR-8)

Compound (9) (200 mg, 0.5 mmol) and β-Alanine (270 mg, 3 mmol) were added to a mixture of ethanol (20 mL) and water (2 mL). Triethylamine (1 mL, 7 mmol) was added and the reaction stirred at room temperature overnight. Solvent was evaporated. Ethyl acetate (5 mL) and acetonitrile (25 mL) were added and the precipitate was collected and washed with cold ethyl acetate (5 mL). The obtained yellow solid was dried under vacuum to give 213 mg (90%) of compound (VOR-8). Compound (VOR-8) had the m/e=464 (M+1). See FIG. 5.

Example 5

Preparation Activated Haptens (6) and (15)

To dried DMF (750 µL) was added EDAC (11.5 mg, 60 mmol), NHS (7.0 mg, 60 mmol), and hapten compound (VOR-5) (25.6 mg, 55 mmol) at room temperature. The mixture was stirred 16 hours to form compound (6). Ester formation was monitored by TLC analysis. The activated hapten (6) was used for the next reaction. Hapten compound (VOR-8) was activated to the NHS ester form compound (15) using similar procedures as described above. See FIGS. 4 and 6.

Example 6

Preparation Enzyme Conjugates (VOR-5 G6PDH) and (VOR-8 G6PDH)

G6PDH (USB) suspended in ammonium sulfate was centrifuged for 15 min at 12,000 rpm. The resulted pellet was reconstituted with phosphate buffer (12.5 mM, pH 7.2). The solution was dialyzed for 2 days at 4° C. against phosphate buffer (12.5 mM, pH 7.2) with three times of buffer exchange. After dialysis, the enzyme solution was transferred to a reaction vial and the pH of the solution was adjusted to 8.7 with sodium bicarbonate buffer (0.4 M, pH 9.4) in the presence of glucose-6-phosphate (G6P, 4.5 mg/mg G6PDH) and NADH (9 mg/mg G6PDH) for the next reaction. See FIGS. 4 and 6.

Activated product compound (6) was added in 5 to 10 µL quantities to a solution of glucose-6-phosphate dehydrogenase (G6PDH, pH 8.7) at ice bath temperature. After the addition of each portion of solution of compound (6) a 2 µL aliquot was taken and was diluted 1:500 with enzyme buffer. A 3 µL aliquot of this diluted conjugation mixture was assayed for enzymatic activity similar to that described in Example 7 below. The reaction was monitored and was stopped at approximately 65% deactivation of enzyme activity. The mixture was desalted with a PD-10 pre-packed Sephadex G-25 (Pharmacia, Inc.) and pre-equilibrated with HEPES buffer (10 mM, pH 6.9, 1 mM EDTA). The reaction mixture was applied to the column and the protein fractions pooled to yield a solution of conjugate (VOR-5 G6PDH). Activated hapten (15) was also conjugated with G6PDH to give conjugate (VOR-8 G6PDH) using a conjugation procedure similar to that described above. See FIGS. 4 and 6.

Example 7

Preparation of Voriconazole-KLH Immunogen (VOR-5-KLH) and (VOR-8 KLH)

Two vials of lyophilized KLH (Pierce) were reconstituted with deionized water each and were pooled, and transferred into a reaction vial. The pH of the KLH solution was adjusted to 8.7 with sodium bicarbonate buffer (0.4 M, pH 9.4). The solution of compound (6) was slowly added (10-20 µL per addition) to the solution of KLH over a period of 4 h at room temperature. After the addition was completed, the mixture was stirred in a 4° C. cold room overnight. This solution was then dialyzed against three changes of HEPES buffer (10 mM, pH 6.9, 1 mM) to give immunogen (VOR-5 KLH). Activated hapten (15) was also conjugated with KLH giving immunogen (VOR-8 KLH) using a conjugation procedure similar to that described above. See FIGS. 4 and 6.

Example 8

Preparation of Polyclonal Antibodies to Voriconazole

Immunogens (VOR-5 KLH and VOR-8 KLH) can be injected into a mouse, sheep or rabbit to raise antibodies. Polyclonal sera from 6 live rabbits were prepared by injecting six animals with immunogen (VOR-5 KLH). Similarly, polyclonal sera from 6 live rabbits were prepared by injecting six animals with immunogen (VOR-8 KLH). This immunogenic formulation included 200 µg of the immunogen for the first immunization and 100 µg for all subsequent immunizations. Regardless of immunogen amount, the formulation was then diluted to 1 mL with sterile saline solution. This solution was then mixed thoroughly with 1 mL of the appropriate adjuvant: Freund's Complete Adjuvant for first immunization or Freund's Incomplete Adjuvant for subsequent immunizations. The stable emulsion was subsequently injected subcutaneously with a 19×1½ needle into New Zealand white rabbits. Injections were made at 3-4 week intervals. Bleeds of the immunized rabbits were taken from the central ear artery using a 19×1 needle. Blood was left to clot at 37° C. overnight, at which point the serum was poured off and centrifuged. Preservatives were added in order to form the polyclonal antibody material. Rabbit polyclonal antibodies to voriconazole produced by the above procedure immunized with immunogen (VOR-5 KLH) were designated as #15395, #15396, #15396, #15398, #15399, and #15400 and rabbits immunized with immunogen (VOR-8 KLH) were designated as #15457, #15458, #15459, #15460, #15461, and #15462.

Rabbit polyclonal antibody Ab15461(P3) was used in examples below.

Rabbit polyclonal antibody Ab15461(P3) was used to measure a substantial change in enzyme activity, generate a calibration curve, and evaluate assay precision, accuracy and specificity. The antibody was added into the antibody diluent to prepare the antibody reagent. The antibody reagent consisted of antibody as prepared above, buffer, stabilizers, preservatives, and the substrates for the enzyme conjugate nicotinamide adenine dinucleotide ($NAD^+$) and glucose-6-phosphate. Enzyme conjugate including compound VOR-8 G6PDH was added into the conjugate diluent to prepare the enzyme conjugate reagent. The enzyme conjugate reagent included the conjugate, buffer, stabilizers and preservatives. Enzyme conjugate VOR-8 G6PDH was used with rabbit polyclonal antibody Ab15461(P3) in examples below. This technique is generally applicable to produce polyclonal antibodies to voriconazole derivatives and assess their utility.

Example 9

Preparation of Monoclonal Antibodies to Voriconazole

Monoclonal antibodies are prepared using standard hybridoma procedures as described in detail (Kohler, G. et al., *Nature* 256: 495-497 (1976); Hurrell, Monoclonal Hybridoma Antibodies: Techniques and Applications, CRC Press, Boca Raton, Fla. (1982). This hybridoma technique is generally applicable to produce monoclonal antibodies to the voriconazole derivatives.

Example 10

Assay for the Detection of Voriconazole

The voriconazole antibodies and enzyme conjugates in accordance with embodiments of the present disclosure may be employed in assays for the detection of voriconazole. Immunogens (VOR-5 KLH and VOR-8 KLH) may be injected into a mouse, rabbit or sheep to raise antibodies. Antibodies may be screened by known methods, and evaluating properties such as specificity, conjugate inhibition, calibration curve size and cross-reactivity.

The obtained antibody is added into the antibody diluent to prepare the antibody reagent. The antibody reagent includes antibody as prepared above, buffer, stabilizers, preservatives, and the substrates for the enzyme conjugate $NAD^+$ and glucose 6 phosphate. Enzyme conjugate including compound (VOR-5 and VOR-8) and G6PDH or a label protein including alkaline phosphatase, β-galactosidase and horse radish peroxidase is spiked into the conjugate reagent to prepare the enzyme conjugate reagent. The enzyme conjugate reagent includes the conjugate, buffer, stabilizers and preservatives.

The voriconazole antibodies and enzyme conjugates may be used in a homogeneous assay format to detect voriconazole samples. An instrument useful to set up the assay is Hitachi 917 Analyzer (Roche). Voriconazole containing sample is incubated with antibody reagent followed by the addition of the enzyme conjugate reagent. The enzyme conjugate activity decreases upon binding to the antibody. The enzyme conjugate, which is not bound to the antibody, catalyzes the oxidation of glucose 6-phosphate (G6P). The oxidation of G6P is coupled with the reduction of $NAD^+$ to NADH, which can be measured at 340 nm. The change in the absorbance at 340 nm can be measured spectrophotometrically. The voriconazole concentration in a sample can be measured in terms of G6PDH activity. The increase in the rate at 340 nm is due to the formation of NADH and is proportional to the enzyme conjugate activity. An assay curve is generated using voriconazole added into serum negative for voriconazole. The assay rate increases with increasing the concentration of free drug in the sample.

Example 11

Calibration Curve

Figure 8:
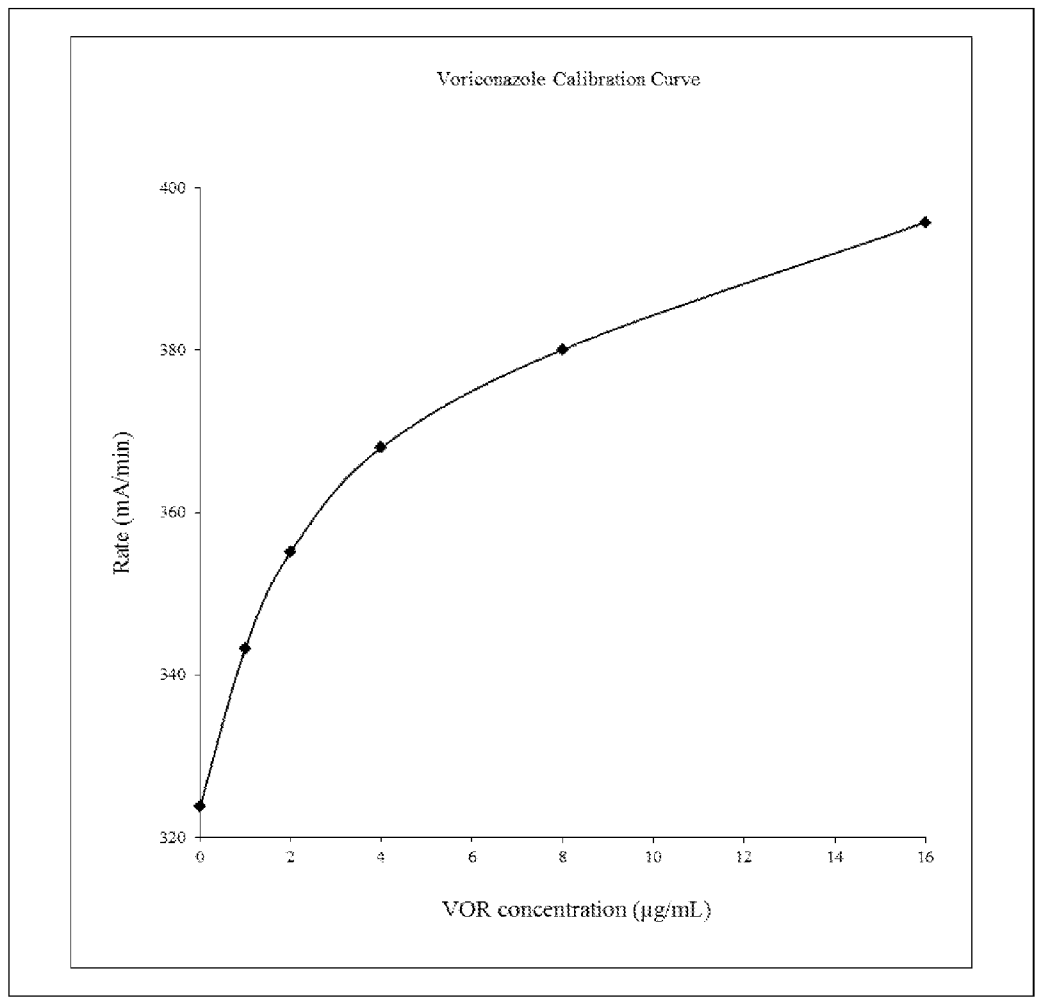
FIG. 8 shows a calibration curve for a competitive homogeneous immunoassay for voriconazole in pooled human serum calibrator matrix using a Roche Hitachi 917 automated clinical chemistry analyzer, according to embodiments of the present disclosure.
Figure 9:
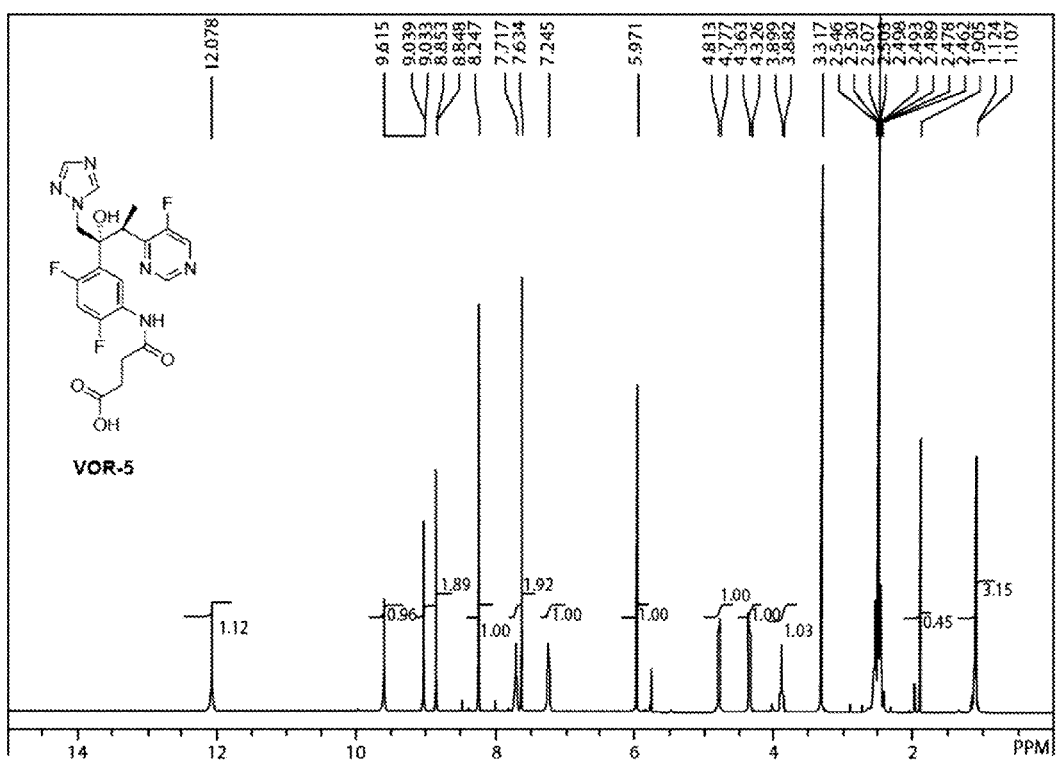
FIG. 9 shows a $^1$HNMR spectrum of voriconazole hapten (VOR-5), according to embodiments of the present disclosure.
Figure 10:
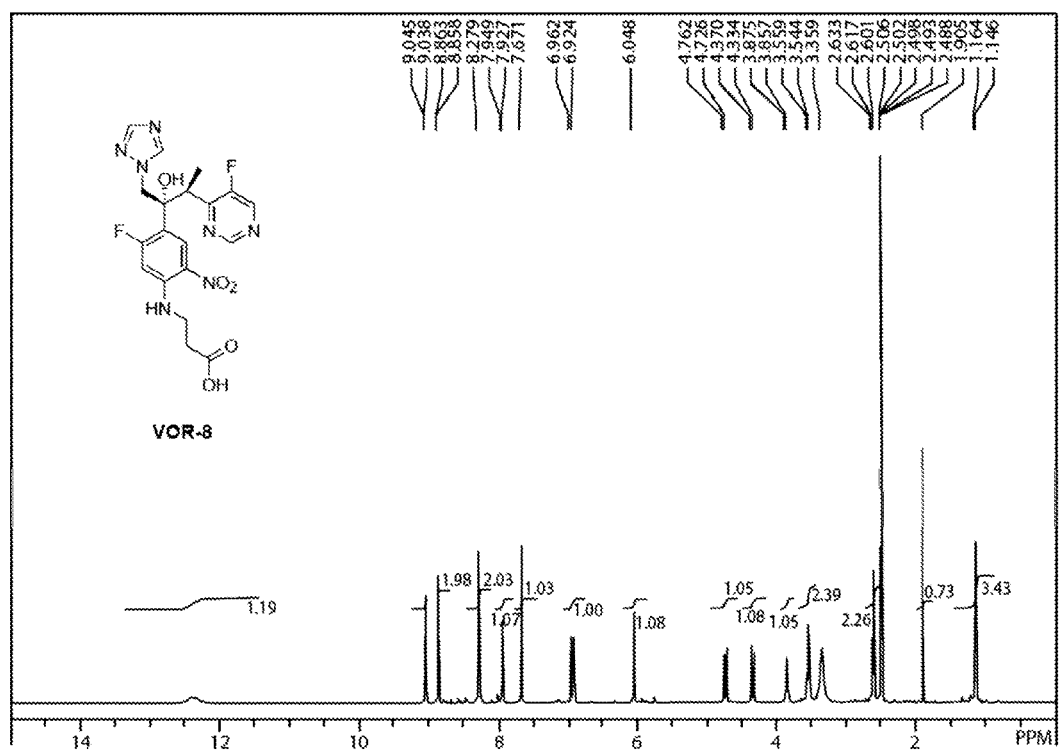
FIG. 10 shows a $^1$HNMR spectrum of voriconazole hapten (VOR-8), according to embodiments of the present disclosure.

Voriconazole was dissolved in methanol to give a stock solution of 1000 µg/mL. Pooled human serum was aliquoted in 10 mL portions. Voriconazole stock solution was added to the aliquots of human serum in preparing a series of known concentrations of voriconazole calibrators ranging from 0 to 16 µg/mL. The assay was performed using Enzyme Conjugate Reagent NB051:79 containing conjugate VOR-8 G6PDH and Antibody Reagent NB051:79 containing antibody Ab15461(P3). Calibration curves were generated on the HITACHI 917 automated clinical chemistry analyzer, as described in Example 10 by measuring each level in duplicate. An example of these calibrator rates is shown in Table 1 and the graph is shown in FIG. 8.

TABLE 1

Typical Calibration Curve Rates

| Voriconazole Conc. (µg/mL) | Reaction Rate (mA/min) Average of Duplicates |
|---|---|
| 0.00 | 306.9 |
| 1.0 | 327.2 |
| 2.0 | 337.4 |
| 4.0 | 349.6 |
| 8.0 | 362.4 |
| 16.0 | 380.4 |

Example 12

Specificity of the Immunoassay in the Presence of N-oxide Voriconazole, a Voriconazole Metabolite The major metabolic pathway of voriconazole is an enzymatic oxidation of voriconazole. The N-oxide voriconazole metabolite displays weak antifungal activity, being 100-fold less potent than the parent drug in vitro (Roffey, et al., Drug Metabolism and Disposition, 31(6):731-781, 2003). The voriconazole metabolite, N-oxide voriconazole was tested in the immunoassay for potential cross reactivity. To human serum negative for voriconazole and N-oxide voriconazole metabolite was added voriconazole dissolved in methanol to achieve a concentration of 5.0 µg/mL of voriconazole. To a second sample was added N-oxide voriconazole dissolved in methanol to achieve a concentration of 50 µg/mL N-oxide voriconazole. To a third sample was added 5.0 µg/mL of voriconazole plus 50 µg/mL N-oxide voriconazole.

The assay was calibrated as described in Example 11 using Enzyme Conjugate Reagent NB051:79 containing conjugate VOR-8 G6PDH and Antibody Reagent NB051:79 containing antibody Ab15461(P3). The testing was performed on the HITACHI 917. The samples were quantified from the calibration curve generated. As shown in Table 2, antibody Ab15461(P3) does not cross react significantly with voriconazole N-oxide metabolite, indicating a highly specific antibody was produced.

TABLE 2

Crossreactivity to N-oxide Voriconazole Metabolite
% Crossreactivity = 100 × (mean value Test − mean value Control) ÷ (Conc. Compound Tested)

| Sample | Crossreactivity (%) |
|---|---|
| Voriconazole (10 µg/mL) | 6.7 |
| Voriconazole (10 µg/mL) + Vor-N-Oxide (5 µg/mL) | |

TABLE 2-continued

Crossreactivity to N-oxide Voriconazole Metabolite
% Crossreactivity = 100 × (mean value Test − mean value Control) ÷ (Conc. Compound Tested)

| Sample | Crossreactivity (%) |
|---|---|
| Voriconazole (10 µg/mL) | 6.7 |
| Voriconazole (10 µg/mL) + Vor-N-Oxide (15 µg/mL) | |

Example 13

Specificity of the Immunoassay in the Presence of Other Azole Antifungals

To human serum negative for antifungal azoles was added voriconazole dissolved in methanol to achieve a concentration of 5.0 µg/mL of voriconazole. To a second sample was added fluconazole dissolved in methanol to achieve a concentration of 50 µg/mL fluconazole. Similarly, itraconazole and posaconazole dissolved in methanol were added to a third and fourth sample, respectively, to achieve a concentration of 50 µg/mL in each sample.

The assay was calibrated as described in Example 11 using Enzyme Conjugate Reagent NB051:79 containing conjugate VOR-8 G6PDH and Antibody Reagent NB051:79 containing antibody Ab15461(P3). The testing was performed on the HITACHI 917. The samples were quantified from the calibration curve generated. As shown in Table 3, antibody Ab15461(P3). did not significantly crossreact with fluconazole, itraconazole and posaconazole, indicating a highly specific antibody was produced.

TABLE 3

Crossreactivity to Antifungal Triazoles
% Crossreactivity = 100 × (mean value Test − mean value Control) ÷ (Conc. Compound Tested)

| Sample | Crossreactivity (%) |
|---|---|
| Voriconazole (10 µg/mL) | 1.2 |
| Voriconazole (10 µg/mL) + Itrconazole (20 µg/mL) | |
| Voriconazole (10 µg/mL) | 2.7 |
| Voriconazole (10 µg/mL) + Fluconazole (20 µg/mL) | |
| Voriconazole (10 µg/mL) | −2.5 |
| Voriconazole (10 µg/mL) + Posaconazole (20 µg/mL) | |

The preceding merely illustrates the principles of the embodiments of the present disclosure. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the embodiments and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

What is claimed is:

1. A compound of the formula:

wherein
Q is —NO₂; and
Z is selected from the group consisting of hydrogen, —OH, —SH, —S-acyl; —O-lower alkyl, halogen, —NH₂, epoxy, maleimidyl, haloacetamide, carboxyl, activated carboxyl, an immunogenic carrier and a label, and
salts thereof.

2. The compound of claim 1, wherein the immunogenic carrier is a protein.

3. The compound of claim 2, wherein the protein is selected from the group consisting of hemocyanins, globulins and albumins.

4. The compound of claim 3, wherein the protein is bovine serum albumin (BSA) or keyhole limpet hemocyanin (KLH).

5. The compound of claim 1, wherein the immunogenic carrier is a polysaccharide.

6. The compound of claim 1, wherein the label is an enzyme.

7. The compound of claim 6, wherein the enzyme is selected from the group consisting of glucose-6-phosphate dehydrogenase (G6PDH), alkaline phosphatase, (β-galactosidase, and horse radish peroxidase.

8. The compound of claim 7, wherein the enzyme is glucose-6-phosphate dehydrogenase (G6PDH).

9. The compound of claim 1, wherein the activated carboxyl group is selected from the group consisting of hydroxysuccinimidyl, succinimidyl, carbonate, anhydride, and imidate.

10. An isolated polyclonal antibody that binds an epitope present in voriconazole, wherein the isolated polyclonal antibody preferentially binds to voriconazole in the presence of a compound of the formula:

(VOR-8 G6PDH)

wherein Q is —NO₂,
wherein the isolated polyclonal antibody has a cross-reactivity with voriconazole N-oxide of less than 10% with respect to binding to voriconazole, and a cross-reactivity with fluconazole, itraconazole and posaconazole of less than 3% each with respect to binding to voriconazole, wherein said cross-reactivities are measured in the presence of VOR-8 G6PDH.

11. A kit for detecting voriconazole in a sample, said kit comprising:
the antibody of claim 10; and
instructions for an assay for detecting voriconazole.

12. The kit of claim 11, further comprising one or more ancillary reagents for detecting a complex of said antibody and voriconazole.

13. The kit of claim 11, further comprising a label conjugate, wherein the label conjugate is VOR-8 G6PDH.

14. A method for detecting voriconazole, said method comprising:
combining in a reaction mixture a sample suspected of containing voriconazole with the antibody of claim 10; and
detecting the presence or absence of a complex comprising said voriconazole and said antibody,
wherein the presence of the complex indicates the presence of voriconazole in said sample.

15. The method of claim 14, wherein the reaction mixture comprises a label conjugate, wherein the label conjugate is VOR-8 G6PDH.

16. The method of claim 15, wherein the detecting comprises determining the presence of an enzymatic reaction product of VOR-8 G6PDH.

* * * * *